(12) United States Patent
Thayumanavan et al.

(10) Patent No.: US 9,999,599 B2
(45) Date of Patent: Jun. 19, 2018

(54) POLYMER-POLYMER COMPOSITE NANOASSEMBLIES AND APPLICATIONS THEREOF

(71) Applicant: University of Massachusetts, Boston, MA (US)

(72) Inventors: Sankaran Thayumanavan, Amherst, MA (US); Conghui Yuan, Amherst, MA (US)

(73) Assignee: University of Massachusetts, Boston, MA (US)

( * ) Notice: Subject to any disclaimer, the term of this patent is extended or adjusted under 35 U.S.C. 154(b) by 437 days.

(21) Appl. No.: 14/421,875

(22) PCT Filed: Sep. 10, 2013

(86) PCT No.: PCT/US2013/058931
§ 371 (c)(1),
(2) Date: Feb. 16, 2015

(87) PCT Pub. No.: WO2014/043084
PCT Pub. Date: Mar. 20, 2014

(65) Prior Publication Data
US 2015/0202163 A1    Jul. 23, 2015

Related U.S. Application Data

(60) Provisional application No. 61/699,764, filed on Sep. 11, 2012.

(51) Int. Cl.
| | |
|---|---|
| *A61K 9/51* | (2006.01) |
| *A61K 47/32* | (2006.01) |
| *A61K 45/06* | (2006.01) |
| *A61K 9/107* | (2006.01) |
| *A61K 47/69* | (2017.01) |
| *B82Y 5/00* | (2011.01) |

(52) U.S. Cl.
CPC .............. *A61K 9/51* (2013.01); *A61K 9/1075* (2013.01); *A61K 9/5138* (2013.01); *A61K 45/06* (2013.01); *A61K 47/32* (2013.01); *A61K 47/6903* (2017.08); *B82Y 5/00* (2013.01)

(58) Field of Classification Search
None
See application file for complete search history.

(56) References Cited

U.S. PATENT DOCUMENTS

| | | | | |
|---|---|---|---|---|
| 2004/0234597 | A1* | 11/2004 | Shefer | A61K 9/1635 424/468 |
| 2005/0169882 | A1* | 8/2005 | Lowe | A61K 9/06 424/78.27 |
| 2011/0182987 | A1* | 7/2011 | Bawa | A61K 9/209 424/464 |

* cited by examiner

*Primary Examiner* — Robert A Wax
*Assistant Examiner* — Randeep Singh
(74) *Attorney, Agent, or Firm* — Milstein Zhang & Wu LLC

(57) ABSTRACT

The invention provides novel nanoscale delivery vehicles and composite nanoassemblies built from distinct nanoassembly units (e.g., block copolymer micelles and nanogels) with stoichiometric control. These intelligent composite nanoassemblies independently retain the key features of the nanoassembly units and greatly expand the potential functional features attainable based on the surface functionalization. The invention provides a novel approach to constructing nano-vehicles with controllable morphology based on combination of cooperative releasing mechanisms (e.g., redox sensitive nanogels and pH sensitive micelles). Two kinds of guests can be seperately and stably encapsulated in the composite nanocontainers, and then released sequentially under the stimulation of pH change and reduced glutathione.

12 Claims, 22 Drawing Sheets

POLYMER-POLYMER COMPOSITE NANOASSEMBLIES AND APPLICATIONS THEREOF

PRIORITY CLAIMS AND RELATED PATENT APPLICATIONS

This application is the U.S. national phase of and claims the benefit of priority from PCT/US13/58931, filed Sep. 10, 2013, which claims the benefit of priority from U.S. Provisional Application Ser. No. 61/699,764, filed on Sep. 11, 2012, the entire content of each of which is incorporated herein by reference in its entirety.

GOVERNMENT RIGHTS

The United States Government has certain rights to the invention pursuant to Grant No. W911NF1010313 from the U.S. Army Research Office to the University of Massachusetts.

TECHNICAL FIELDS OF THE INVENTION

The invention generally relates to polymer-based nanostructures, methods of making and using the same. More particularly, the invention relates to novel, functionalized polymer nano-composites and nano-delivery vehicles that are derived from two or more distinct component nanoassemblies and are useful in diverse fields including specialty materials, drug delivery and diagnostics.

BACKGROUND OF THE INVENTION

Self-organization of polymers has been utilized in obtaining well-defined supramolecular assemblies such as micelles, vesicles, fibers, helical superstructures, nanoparticles and macroscopic tubes. (Zhang, et al. 1995 *Science* 268, 1728; Zhang, et al. 1996 *Science* 272, 1777; Hest, et al. 1995 *Science* 268, 1592; Discher, et al. 2002 *Science* 297, 967; Hartegrink, et al. 2001 *Science* 294, 1684; Claussen, et al. 2003 *J. Am. Chem. Soc.* 125, 12680; Conrnelissen, et al. 1998 *Science,* 280, 1427; McCarthy, et al. 2005 *Nano Lett.* 12, 2552; Yan, et al. 2004 *Science,* 303, 65.) These self-assembled superstructures are of interest in a variety of areas ranging from material science to biology. (Stupp, et al. 1997 *Science* 277, 1242: Savic, et al. 2003 *Science* 300, 615.)

A daunting challenge remains in developing nanoscale polymeric assemblies that combine two or more of nanoassemblies to achieve a hybrid or a composite nanostructure. The difficulties are primarily due to the structural requirements associated with the formation of assemblies. Most supramolecular assemblies are achieved by balancing the presence of two incompatible functional groups within the same molecule. (Israelachvili, et al. 1976 *J. Chem. Soc., Faraday Trans.* 2, 72, 1525; Discher, et al. 1999 *Science* 284, 1143; Tang, et al. 2008 *Science* 322, 429.) When this balance is disturbed, the fidelity of assembly is affected. Classical example includes the need for hydrophilic-lipophilic balance in amphiphilic molecules to maintain well-defined nanoscale assemblies. (Azagarsamy, et al. 2010 *J. Am. Chem. Soc.* 132, 4550; Azagarsamy, et al. 2009 *J. Am. Chem. Soc.* 131, 14184; Amir, et al. 2009 *J. Am. Chem. Soc.* 131, 13949; Guo, et al. 2012 *J. Am. Chem. Soc.* 134, 10244.) A major difficulty arises from the fact that composite nanostructures, made from two different nanoassemblies, would likely disturb that critical balance needed for the fidelity of the individual nanostructures.

Delivering guest molecules accurately to target sites with controlled release is of particular importance in medical therapeutics and biomedical diagnostics. (Allen, et al. 2004 *Science* 303, 1818-1822; Farokhzad, et al. 2009 *ACS Nano* 3, 16-20; Rozhkova 2011 *Adv. Mater.* 23, H136-H150.) A variety of nanocontainers have been studied for controllable delivery since nanocontainers have the potential to administer guest molecules, as well as enhance the therapeutic effect while possessing low inherent toxicity. (Pan, et al. 2012 *J. Am. Chem. Soc.* 134, 5722-5725; Shiah, et al. 1999 *J. Control Release* 61, 145-157; Bae, et al. 2005 *Bioconjug. Chem.* 16, 122-130; Duncan 2003 *Nature Rev. Drug. Discov.* 2, 347-360; Rothenfluh, et al. 2008 *Nature Mater.* 7, 248-254.)

Water-soluble polymer nanoparticles, such as micelles, nanogels and polymersomes, are promising candidates for nanocontainers due to their stability profile, high biocompatibility and facile functionalization. (Christian, et al. 2009 *Nature Mater.* 8, 243-249; Kataoka, et al. 2001 *Adv. Drug Deliv. Rev.* 47, 113-131; Cabral, et al. 2007 *J. Control. Release* 121, 146-155; Matsumura, et al. 2009 *Cancer Sci.* 100, 572-579; Plummer, et al. 2011 *Br. J. Cancer* 104, 593-598; Aliabadi, et al. 2006 *Expert Opin. Drug Deliv.* 3, 139-162; Nishiyama, et al. 2006 *Pharmacol. Therapeut.* 112, 630-648; Cabral, et al. 2001 *Nature Nanotech.* 6, 815-823; Nochi, et al. 2010 *Nature Mater.* 9, 572-578; Ryu, et al. 2010 *J. Am. Chem. Soc.* 132, 17227-17235; Oh, et al. 2008 *Prog. Polym. Sci.* 33, 448-477; Akiyoshi, et al. 1997 *Macromolecules* 30, 857-861; Kageyama, et al. 2008 *Cancer Sci.* 99, 601-607; Ryu, et al. 2010 *J. Am, Chem. Soc.* 132, 8246-8247; Discher, et al. 2002 *Science* 297, 967-973; Meng, et al. 2009 *Biomacromolecules* 10, 197-209; Iatrou, et al. 2007 *Biomacromolecules* 8, 2173-2181; Zhou, et al. 2005 *J. Am. Chem. Soc.* 127, 10468-10469.)

Nanocontainers are typically constructed by both hydrophobic and hydrophilic components, which endow them with high hydrophobic guest encapsulation capability and excellent solubility in water. Encapsulation and release of the guest are two faces of one contradiction. Stable encapsulation easily results in an extremely low release rate, while desirable release rate is always a consequence of unstable encapsulation. To resolve this conflict, nanocarriers with stimulus-response properties have been designed to achieve triggered and targeted release.

Several strategies have been investigated for the triggered release, such as pH, temperature, light and redox sensitivities. (Du, et al. 2005 *J. Am. Chem. Soc.* 127, 17982-17983; Kakizawa, et al. 2002 *Adv. Drug Deliver. Rev.* 54, 203-222; Lee. et al. 2007 *J. Am. Chem. Soc.* 129, 15096-15097; Martien, et al. 2010 *Nature Mater.* 9, 101-113; Li, et al. 2006 *Angew. Chem. Int. Ed.* 45, 5792-5795; Qin, et al. 2006 *Adv. Mater.* 18, 2905-2909; Goodwin, et al. 20051 *Am. Chem. Soc.* 127, 9952-9953; Kostiainen, et al. 2010 *Nature Chem.* 2, 394-399; Power-Billard, et al. 2004 *Angew. Chem., Int. Ed.* 43, 1260-1264; Lin, et al. 2007 *Bioconjugate Chem.* 18, 138-145; Thorpe, et al. 1987 *Cancer Res.* 15, 5924-5931; Klaikherd, et al. 2009 *J. Am. Chem. Soc.* 131, 4830-4838.) Unfortunately, many of these systems just respond automatically to the environmental signals and make some corresponding changes in chemical or physical properties, which can easily cause inaccurate and uncontrollable delivery.

To overcome these drawbacks, researchers have tried to install guiding devices on nanocontainers. It has been reported that decorating the surface of nanocontainers with ligands, such as peptide, protein and antibody, can assist selective targeted delivery. This strategy, however, demands a high degree of control over ligand density to achieve high selectivity. (Rothenfluh, et al. 2008 *Nature Mater.* 7, 248-254; Ashley, et al. 2011 *Nature Mater.* 10, 389-397; Strauch, et al. 2011 *J. Am. Chem. Soc.* 133, 16346-16349; Farokhzad, et al. 2006 *Proc. Natl Acad. Sci. USA* 103, 6315-6320; Pastan, et al. 2006 *Nat. Rev. Cancer* 6, 559-565.) For example, in the tumor cell targeted delivery system, a high density of targeted ligand is required to improve affinity and delivery efficiency. On the other hand, a high ligand density can enhance nonspecific interations with endothelial and other non-cancer cells and increase immunogenicity, leading to opsonization-mediated clearance of nanocontainers. (Peer, et al. 2007 *Nature Nanotech.* 2, 751-760; Ferrari 2008 *Nature Nanotech.* 3, 131-132.)

Thus, a major unmet need remains for an intelligent nano-vehicle with accurate and controlled delivery of multiple guests. In particular, it is highly desirable to have composite supramolecular nanostructures that are hybrids of and independently retain key features in two or more distinct nanoassembly components.

SUMMARY OF THE INVENTION

The invention is based, in part, on the unexpected discovery of novel nano-vehicles and composite nanoassemblies constructed from distinct component nanoassembly units (e.g., block copolymer micelles and polymeric nanogels). These nano-vehicles and composite nanoassemblies independently retain the key features of the component nanoassembly units. These intelligent nano-vehicles and composite nanoassemblies may be built from two or more diverse types of nanoparticles and, therefore, greatly expand the potential functionalities attainable based on the surface functional groups of the component nanoparticles, which can be engineered to work synergistically with one another.

A novel approach is provided herein that establishes a new paradigm for designing and constructing nano-vehicles (e.g., nano-containers) with controllable morphology based on combination of orthogonal releasing mechanisms (e.g., redox sensitive nanogels and pH sensitive micelles). Two or more kinds of guests (e.g., therapeutic agents) can be seperately and stably encapsulated in the nano-vehicles, and then released simultaneously or sequentially in a controlled fashion (e.g., triggered by a pH change and reduced glutathione). The intelligent nanocontainers of the invention can be constructed from a combination of two or more different polymeric nanostructures with stoichiometric control (e.g., polymeric nanogels and polymeric micelles). These unique functionalities in combination allow them to be adaptable to a variety of applications, for example, the stepwise delivery of different drug molecules at a specific location with independently controlled cargo release.

In one aspect, the invention generally relates to a nano-vehicle carrying two molecular cargos. The nano-vehicle includes: (1) a first nanoassembly comprising a first molecular cargo encapsulated stably therein and is individually addressable by a first biological or chemical intervention resulting in a structural change therein and release of the first molecular cargo from the first nanoassembly; and (2) a second nanoassembly comprising a second molecular cargo encapsulated stably therein and is individually addressable by a second biological or chemical intervention resulting in a structural change therein and release of the second molecular cargo from the second nanoassembly. The first nanoassembly and the second nanoassembly are non-covalently or covalently associated in a stoichiometric controlled ratio to form the nano-vehicle. The first nanoassembly and the second nanoassembly are structurally distinctive at the nanoscale.

In certain preferred embodiments, wherein the first nanoassembly is a polymeric nanogel and the second nanoassembly is a polymeric micelle. For example, the polymeric nanogel is formed from a random copolymer via a controlled crosslinking and the polymeric micelle may be formed from a block copolymer at a controlled pH.

In another aspect, the invention generally relates to a composite nanoassembly that includes two, three or more types of unit nanoassemblies. Each unit nanoassembly type is structurally distinctive at the nanoscale and is individually addressable by biological or chemical intervention resulting in a structural change therein. The biological or chemical intervention for one type of unit nanoassembly is orthogonal to that for other unit nanoassembly types thereby allowing controlled intervention. Thus, the occurrence of a biological or chemical intervention directed at one nanoassembly does not interfere with the stability of the other unit nanoassemblies.

In yet another aspect, the invention generally relates to a method for controlled delivery of two or more distinctive agents to a target biological site. The method includes: (1) providing a composite nanoassembly comprising two or more types of unit nanoassemblies. Each unit nanoassembly type is structurally distinctive and is individually addressable by a biological or chemical intervention resulting in a structural change therein. Each unit nanoassembly type comprises a distinctive agent encapsulated stably therein; (2) delivering the composite nanoassembly to the target biological site; (3) causing a first biological or chemical intervention resulting in a structural change in the first unit nanoassembly type and destabilization of the encapsulation of the first distinctive agent therein, resulting in release of the first distinctive agent therefrom; and (4) causing a second biological or chemical intervention resulting in a structural change in the second unit nanoassembly type and destabilization of the encapsulation of the second distinctive agent therein, resulting in release of the second distinctive agent therefrom.

In certain preferred embodiments, the target biological site is inside a tumor cell. The composite nanoassembly may be designed to be preferably taken up by tumor cells as compared to non-tumor under a physiological condition. In certain preferred embodiments, each of the first guest molecule and the second guest molecule is selected from a biologically active therapeutic, diagnostic or imaging agent, for example, an antitumor agent.

DETAILED DESCRIPTION OF THE INVENTION

Figure 1:
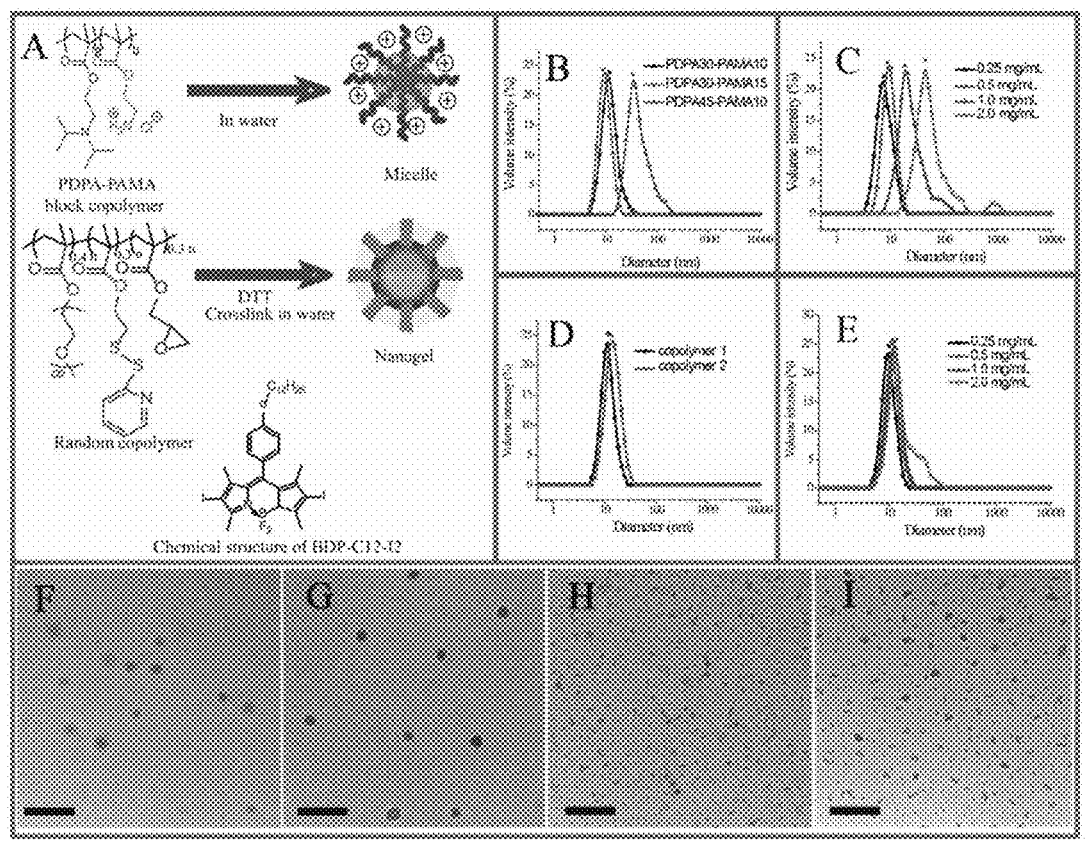
FIG. 1. Micelles and nanogels formation processes from amphiphilic block copolymer and random copolymer, and chemical structure of BDP-C12-I2 (A); diameter of micelles assembled from block copolymers with different ratios of hydrophilic and hydrophobic segments (B) and various concentrations (C); diameter of nanogels formed from random copolymers with different molecular weights (D, the molecular weights of copolymer 1 and copolymer 2 were shown in FIG. 7 and Table 1) and different concentrations (E). TEM images of micelles before (F) and after (G) encapsulation of BDP-C12-I2, and nanogels before (H) and after (I) encapsulation of BDP-C12-I2. The micelles were formed from 2.0 mg/mL of PDPA$_{30}$-b-PAMA$_{15}$ block copolymer solution, while the nanogels were prepared by 2.0 mg/mL of random copolymer 1 solution. All scale bars in the TEM images are 100 nm.

The invention provides intelligent composite nanoassemblies and nano-vehicles from the combination of two or more distinctive nanostructures, for example, nanogels and micelles. An important application of this invention is the targeted delivery of two or more guest molecules (e.g., therapeutic agents) for controlled simultaneous or sequential release at target site(s) (e.g., inside a tumor cell). For example, two nanoassemblies can be covalently attached to each other, wherein one nanostructure component (e.g., the micelles) are pH sensitive and another nanostructure component (e.g., the nanogels) are redox sensitive. The properties of the combined composition may be fine-tuned, for example, by tuning the ratio of the micelles to the nanogels, modifying the molecular structures of the polymers used to construct the nanogels and the micelles, as well as the release triggering mechanisms.

A major challenge remains in accurately delivering drugs to tumor cells. Sequential delivery of two or even more types of guest molecules is desirable because many diseases, such as cancer, is better treated simultaneously by a combination of drugs. (Tilakaratne, et al. 2007 *Biomaterials* 28, 89-98; Patil, et al. 2007 *J. Controlled Release* 117, 68-79.) For a relatively simple sequential delivery system, different guests are separately released in different periods under the same stimulus. In a complicated one, each guest is delivered under a specific stimulus and at a specific time. (Sung, et al. 2009 *Biomaterials* 30, 622-631; Zhao, et al. 2009 *J. Am. Chem. Soc.* 131, 8398-8400; Troutman, et al. 2009 *Adv. Mater.* 21, 2334-2338.) The main challenge in the design of sequential delivery containers is to simultaneously encapsulate various guests and release them in an orderly fashion, while preventing them from leaking and mixing with each other.

To illustrate the invention by examples, the surface of the micelles may be functionalized (e.g., with amino groups), and so are the surface of the nanogels (e.g., with epoxy groups). A driving force for the combination of the above-mentioned nanogels and micelles is the chemical reaction between amino and epoxy groups. When encountering weak acid site (e.g., pH around 6.5), the disassembly of the micelles leads to the liberation of nanogel. At the same time, the positive charged block copolymer can attach to the nanogel surface, making the nanogel change from neutral (or slightly negative charged) to positive charged. As a result, the positive charged nanogel can be easily absorbed by the cells in the target sites. Consequently, the positive charges can be deliberately shielded and opportunely exposed.

Thus, for example, a positively charged amine can be buried within the interior of the block copolymer in response to a stimulus (e.g., a pH level). This positive charge revelation can cause the activated uptake of the nanogels on to the cells. Additionally, this approach allows the revelation of a ligand that can recognize the over-expressed receptors on the surface of a cell. The ligand is buried inside the lipophilic block. When the stimulus converts the hydrophobic block to a hydrophilic block, the ligand is revealed on the surface of the nanogel and thus makes it available for recognition-mediated uptake of the cells.

The nanocarriers of the invention (e.g., the micelles and nanogels) are sensitive to different stimuli, making it possible to release two different guest molecules sequentially or simultaneously, making the nano-vehicles of the invention excellent carriers for administration and co-administration of multiple therapeutic, diagnostic or imaging molecules.

The invention delivers a number of advantages. First, composite nanoassemblies and nano-vehicles of the invention can simultaneously deliver two or more types of guest molecules (e.g., antitumor agents). The guest molecules can be independently encapsulated in the micelles and nanogels and controllably released sequentially or simultaneously by controlled release-triggering events. The micelles and nanogels can be sensitive to the same or different stimuli, thus providing excellent complementarity. Second, the dissociation of composite nanoassemblies and the surface charge reversal of the nanogels from negative to positive can take place at the same time. Third, the quantity of the nanogels coating on the micelles, or the quantity of the micelles coating on the nanogels can be adjusted by simply changing their ratio during the composite generation reaction.

Thus, first disclosed herein is a unique, intelligent composite nanoassembly system built from the combination of two or more distinctive nanostructures, for example, nanogels and micelles, with stoichiometric control. For example, the composite nanoassembly may be based on a micellar assembly formed from amphiphilic block copolymers and a nanogel formed from a self-crosslinking polymer assembly. The composite nanoassembly system retains the key features of both assemblies and that these assemblies can be designed to be synergistically effective for a variety of applications. The intelligent composite nanoassembly system provides a unique platform for drug delivery where two or more agents can be sequentially delivered in a controlled fashion.

In one aspect, the invention generally relates to a nano-vehicle carrying two molecular cargos. The nano-vehicle includes: (1) a first nanoassembly comprising a first molecular cargo encapsulated stably therein and is individually addressable by a first biological or chemical intervention resulting in a structural change therein and release of the first molecular cargo from the first nanoassembly; and (2) a second nanoassembly comprising a second molecular cargo encapsulated stably therein and is individually addressable by a second biological or chemical intervention resulting in a structural change therein and release of the second molecular cargo from the second nanoassembly. The first nanoassembly and the second nanoassembly are non-covalently or covalently associated in a stoichiometric controlled ratio to form the nano-vehicle. The first nanoassembly and the second nanoassembly are structurally distinctive at the nanoscale.

It is noted that the terms "first" and "second", as used herein, do not designate the spatial, tempo or functional order or sequence thereof.

In certain preferred embodiments, wherein the first nanoassembly is a polymeric nanogel and the second nanoassembly is a polymeric micelle. For example, the polymeric nanogel is formed from a random copolymer via a controlled crosslinking and the polymeric micelle may be formed from a block copolymer at a controlled pH.

Depending on the application and the nanoassemblies used, the stoichiometric ratio of the first nanoassembly to the second nanoassembly may be from about 1:20 to about 20:1.

The first or the second biological or chemical intervention may be any suitable biological or chemical intervention such as a change in the environment in pH, redox potential, enzymatic activity, protein concentration, light, heat, or mechanical stress. In certain embodiments, the first biological or chemical intervention and the second biological or chemical intervention are the same biological or chemical intervention. In certain embodiments, the first biological or chemical intervention and the second biological or chemical intervention are different same biological or chemical interventions.

The nano-vehicle generally may have a collective diameter from about 10 nm to about 300 nm, for example.

In certain embodiments of the nano-vehicle, each of the first nanoassembly is capable of stably encapsulating from about 0.1 wt % to about 25 wt % of the first molecular cargo, and each of the second nanoassembly is capable of stably encapsulating from about 0.1 wt % to about 25 wt % of the second molecular cargo.

In another aspect, the invention generally relates to a composite nanoassembly that includes two, three or more types of unit nanoassemblies. Each unit nanoassembly type is structurally distinctive at the nanoscale and is individually addressable by biological or chemical intervention resulting in a structural change therein. The biological or chemical intervention for one type of unit nanoassembly is orthogonal to that for other unit nanoassembly types thereby allowing controlled intervention. Thus, the occurrence of a biological or chemical intervention directed at one nanoassembly does not interfere with the stability of the other unit nanoassemblies.

In certain preferred embodiments, the composite nanoassembly includes two types of unit nanoassemblies. The first unit nanoassembly type includes a first guest molecule encapsulated stably therein and is individually addressable by a first biological or chemical intervention. The second unit nanoassembly type includes a second guest molecule encapsulated stably therein is individually addressable by a first biological or chemical intervention.

The first or the second biological or chemical intervention may be any suitable biological or chemical intervention such as a change in the environment in pH, redox potential, enzymatic activity, protein concentration, light, heat, or mechanical stress.

In certain preferred embodiments of the composite nanoassembly, the first unit nanoassembly type is a nanogel type and the second unit nanoassembly is a micelle type. The nanogel may be formed, for example, from a polymer with controlled crosslinking. The polymer may be a copolymer (e.g., a random copolymer, a block copolymer), such as poly(oligoethyleneglycol monomethylether methacrylate-co-glycidyl methacrylate-co-pyridyl disulfide alkyl methacrylate) (examples of alkyl include $C_1$-$C_{12}$ alkyl groups).

The micelle may be formed, for example, from a polymer with controlled pH. The polymer may be a copolymer (e.g., a block copolymer), such as poly((2-(diisopropylamino) alkyl methacrylate-b-2-aminoalkyl methacrylate hydrochloride). (examples of alkyl include $C_1$-$C_{12}$ alkyl groups)

In certain preferred embodiments of the composite nanoassembly, each of the first guest molecule and the second guest molecule is selected from a biologically active therapeutic, diagnostic or imaging agent, for example, an antitumor agent.

The composite nanoassembly can be designed to be preferably taken up by tumor tissue as compared to non-tumor tissue under a physiological condition. The composite nanoassembly can be designed to be preferably taken up by tumor cells as compared to non-tumor cells under a physiological condition. One or more of the unit nanoassemblies can be designed to be preferably taken up by a tumor cell in a physiological environment.

The stoichiometric ratio of the first unit nanoassembly type to the second nanoassembly type may be any suitable ration, for example, from about 1:20 to about 20:1

Each of the first nanoassembly is capable of stably encapsulating from about 0.1 wt % to about 25 wt % of the first molecular cargo, for example. Each of the second nanoassembly is capable of stably encapsulating from about 0.1 wt % to about 25 wt % of the second molecular cargo, for example.

In yet another aspect, the invention generally relates to a method for controlled delivery of two or more distinctive agents to a target biological site. The method includes: (1) providing a composite nanoassembly comprising two or more types of unit nanoassemblies. Each unit nanoassembly type is structurally distinctive and is individually addressable by a biological or chemical intervention resulting in a structural change therein. Each unit nanoassembly type comprises a distinctive agent encapsulated stably therein; (2) delivering the composite nanoassembly to the target biological site; (3) causing a first biological or chemical intervention resulting in a structural change in the first unit nanoassembly type and destabilization of the encapsulation of the first distinctive agent therein, resulting in release of the first distinctive agent therefrom; and (4) causing a second biological or chemical intervention resulting in a structural change in the second unit nanoassembly type and destabilization of the encapsulation of the second distinctive agent therein, resulting in release of the second distinctive agent therefrom.

The terms "first" and "second", as used herein, do not designate the spatial, tempo or functional order or sequence thereof. Thus, for example, the step of "causing a first biological or chemical intervention resulting in a structural change in the first unit nanoassembly type and destabilization of the encapsulation of the first distinctive agent therein, resulting in release of the first distinctive agent therefrom" may occur prior to, concurrently, or after the step of "causing a second biological or chemical intervention resulting in a structural change in the second unit nanoassembly type and destabilization of the encapsulation of the second distinctive agent therein, resulting in release of the second distinctive agent therefrom."

The target biological site may be any suitable biologically relavent location, e.g., inside, outside or the surface of a cell. The target biological site may be inside a tissue or organ.

In certain embodiments, the first biological or chemical intervention and the second biological or chemical intervention are the same biological or chemical intervention. In certain embodiments, the first biological or chemical intervention and the second biological or chemical intervention are different same biological or chemical interventions. In certain embodiments, the first biological or chemical intervention and the second biological or chemical intervention are orthogonal to one another.

In certain preferred embodiments of the method, the target biological site is inside a tumor cell. The composite nanoassembly may be designed to be preferably taken up by tumor cells as compared to non-tumor under a physiological condition. In certain preferred embodiments, each of the first guest molecule and the second guest molecule is selected from a biologically active therapeutic, diagnostic or imaging agent, for example, an antitumor agent.

The first or the second biological or chemical intervention may be any suitable biological or chemical intervention such as a change in the environment in pH, redox potential, enzymatic activity, protein concentration, light, heat, or mechanical stress.

In certain preferred embodiments, the first unit nanoassembly type is a nanogel type and the second unit nanoassembly is a micelle type. The nanogel may be formed, for example, from a polymer with controlled crosslinking. The polymer may be a copolymer (e.g., a random copolymer, a block copolymer), such as poly(oligoethyleneglycol monomethylether methacrylate-co-glycidyl methacrylate-co-pyridyl disulfide alkyl methacrylate). The micelle may be formed, for example, from a polymer with controlled pH. The polymer may be a copolymer (e.g., a block copolymer), such as poly((2-(diisopropylamino) alkyl methacrylate-b-2-aminoalkyl methacrylate hydrochloride) (examples of alkyl include $C_1$-$C_{12}$ alkyl groups). Each of the first nanoassembly is capable of stably encapsulating from about 0.1 wt % to about 25 wt % of the first molecular cargo, for example. Each of the second nanoassembly is capable of stably encapsulating from about 0.1 wt % to about 25 wt % of the second molecular cargo, for example.

In certain embodiments, the copolymer is poly(oligoethyleneglycol monomethylether acrylate-co-glycidyl acrylate-co-coumarinylalkyl acrylate) (examples of alkyl include $C_1$-$C_{12}$ alkyl groups).

The stoichiometric ratio of the first unit nanoassembly type to the second nanoassembly type may be any suitable ratio, for example, from about 1:20 to about 20:1.

Exemplary functional groups for nanogel include amines, epoxides, episulfides, episulfonium ions, aldehydes, ketones, carboxylic acid and its activated esters, isocyanates, isothiocyanates, anhydrides, substituted aziridines including quaternary ammoniums, and catechol. Exemplary functional groups on the block polymers of micelles include: amines, phenols, carboxylic acids, alkoxyamines, N-substituted or N,N-disubstituted hydrazines, substituted imidazole, and boronic acids.

EXAMPLES

Example I. Composite Nanoassemblies from Polymeric Micelles and Nanogels

Poly((2-(diisopropylamino) ethyl methacrylate-b-2-aminoethyl methacrylate hydrochloride) (PDPA-b-PAMA) was used as the block copolymer (FIG. 1A), which was synthesized by atom transfer radical polymerization (ATRP). (Wang, et al. 1995 *Macromolecules* 28, 7901; Patten, et al. 1996 *Science*, 272, 866.) Examination of the supramolecular assembly formed from this amphiphilic polymer in aqueous solution using dynamic light scattering (DLS) revealed that assemblies have diameters ranging from 10 nm to 35 nm (FIG. 1B and FIG. 1C). Since certain amount of dilution would occur during the formation of composite assemblies, the block copolymer assemblies were examined before and after dilution. The assemblies had small perturbations, if any, in size after diluting the solution to half concentration.

Figure 7:
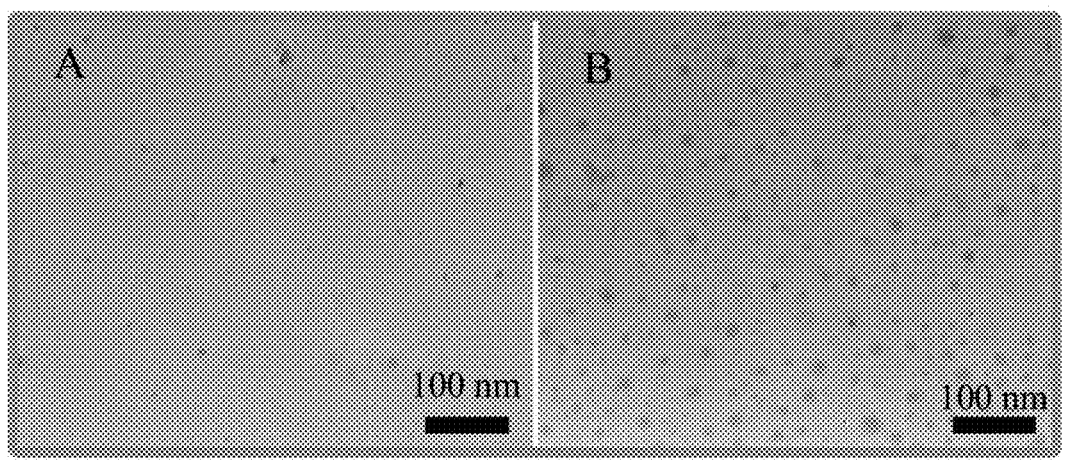
FIG. 7. TEM images of micelles formed from 0.5 mg/mL (A) and 1.0 mg/mL (B) of $PDPA_{30}$-b-$PAMA_{15}$ block copolymer.
Figure 8:
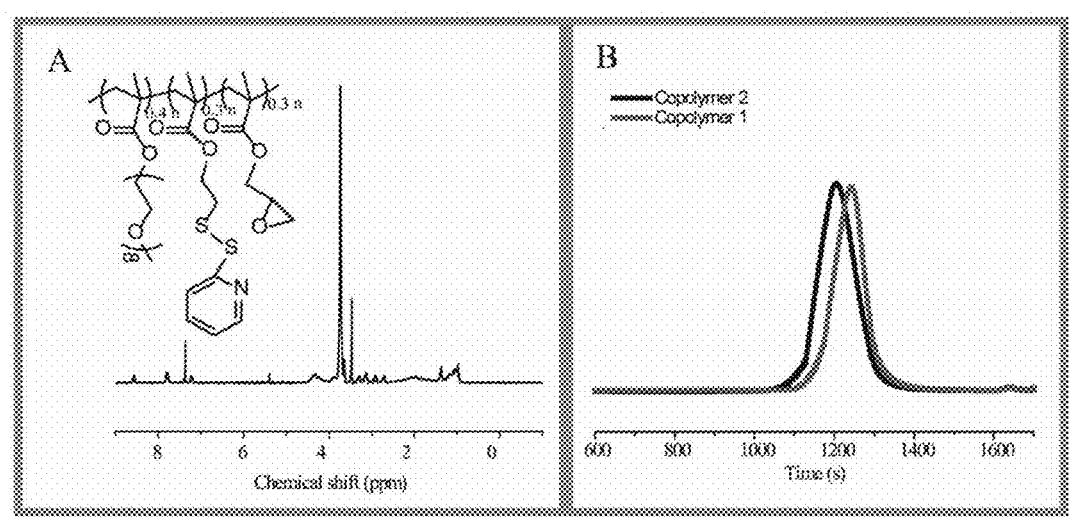
FIG. 8. Chemical structure of random copolymers and $^1$H NMR spectrum of the random copolymer (A) and THF GPC curves of random copolymers synthesized from 4 and 8 h polymerization time (B).
Figure 9:
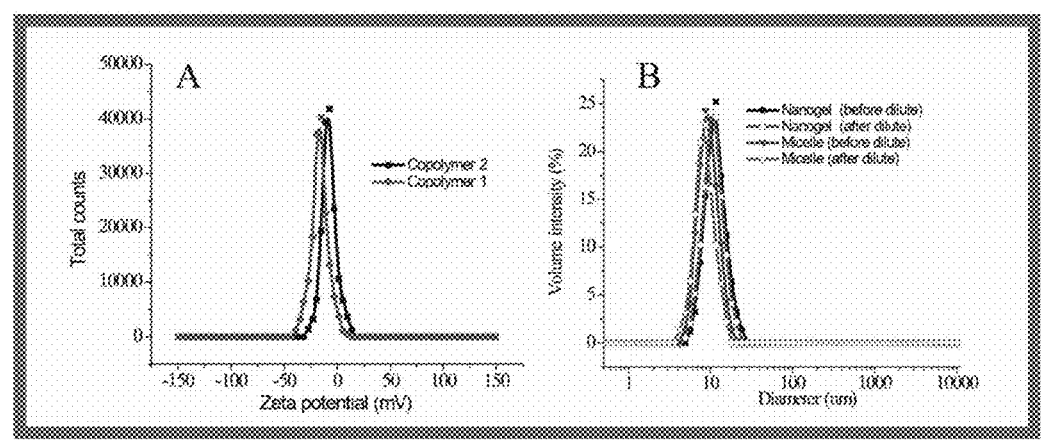
FIG. 9. Zeta potential of nanogels with 0.5 mg/mL concentration (A); diameter of the nanogels (formed from random copolymer 1) and micelles (formed from $PDPA_{30}$-b-$PAMA_{15}$) with 0.5 mg/mL concentration before and after diluting to double volume (B). The nanogels used in these testing were 40% crosslinked.
Figure 10:
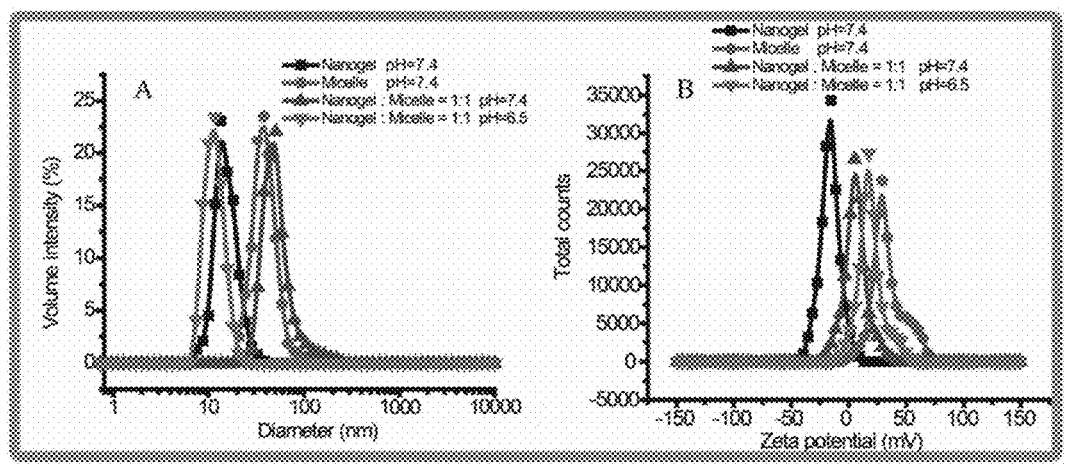
FIG. 10. (A) Diameters of nanogels (■), micelles (●), composite nanoassemblies at pH 7.4 (▲) and 6.5 (▼). (B) Zeta potential of nanogels (■), micelles (●) and the composite nanoassemblies at pH=7.4 (▲) and pH=6.5 (▼). The nanogels and the micelles used here were prepared by 0.5 mg/mL of copolymer 2 and block copolymer $PDPA_{45}$-b-$PAMA_{10}$.
Figure 11:
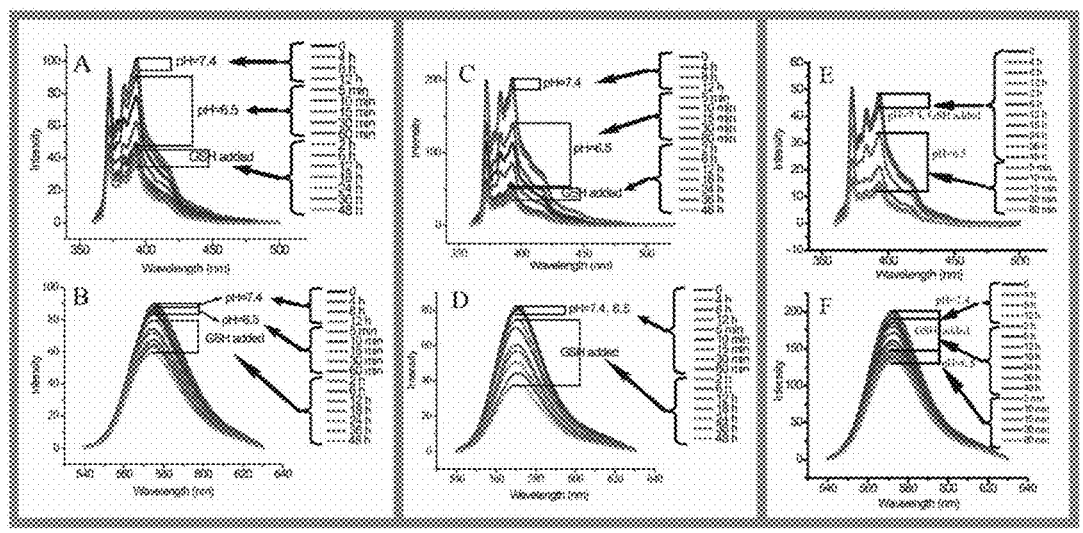
FIG. 11. Fluorescence spectra trace the release of pyrene and DiI from the composite nanoassemblies in response to pH and GSH. In the case of (A), (B) and (C), (D), the composite nanoassembly solution pH was firstly decreased from 7.4 to 6.5, and then GSH (0.1 mM in (A), (B) and 5.0 mM in (C), (D)) was added in the solution. In case of (E) and (F) GSH (0.1 mM) was firstly added to uncrosslink the nanogel, and then the pH of the solution was decreased from 7.4 to 6.5. The composite nanoassemblies were constructed by 9:1 ratio of copolymer 1 nanogels (0.5 mg/mL) and $PDPA_{30}$-b-$PAMA_{15}$ micelles (0.5 mg/mL). All the nanogels used in the release testing were 40% crosslinked. Pyrene was encapsulated in the micelles, while the DiI was encapsulated in nanogels.
Figure 12:
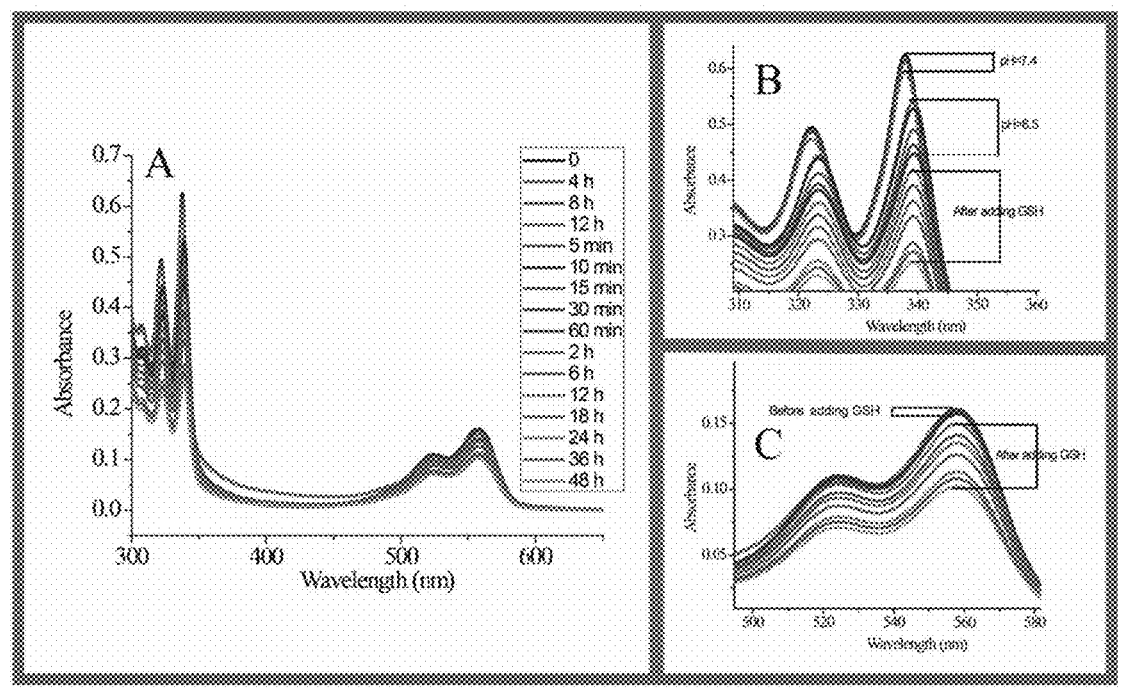
FIG. 12. UV/vis spectra running after the sequential release of pyrene and DiI from the composite nanoassemblies (formed from 9:1 ratio of nanogels and micelles) (A). (B) and (C) are the magnified areas of (A). The nanogels used here are 40% crosslinked from the 0.5 mg/mL of copolymer 1, the micelles are prepared from 0.5 mg/mL of $PDPA_{30}$-b-$PAMA_{15}$ and the GSH added for the release of DiI was 0.1 mM.

Nanogels was prepared from the random copolymer, poly(oligoethyleneglycol monomethylether methacrylate-co-glycidyl methacrylate-co-pyridyl disulfide ethyl methacrylate) (P(EGMA-GMA-PDSEMA)), where PDSEMA monomer was used to generate disulfide crosslinks using a simple D,L-dithiothreitol (DTT)-induced crosslinking reaction (FIG. 1A). (Ryu, et al. 2010 *J. Am. Chem. Soc.* 132, 17227; Ryu, et al. 2010 *J. Am. Chem. Soc.* 132, 8246.) Nanogels of ~10 nm in size were synthesized (FIG. 1D and FIG. 1E), as confirmed by DLS, and since these nanogels are chemically crosslinked, the sizes do not vary upon diluting. The molecular weights of copolymer 1 and copolymer 2 were shown in FIG. 7 and Table 1.

TABLE 1

Summary of $M_n$, $M_w$ and PDI of the random copolymers for nanogels

|  | $M^n$ | $M_w$ | PDI |
| --- | --- | --- | --- |
| Copolymer 1 | 21044 | 26691 | 1.26 |
| Copolymer 2 | 25464 | 35558 | 1.38 |

As shown in FIG. 1F and FIG. 1H, the sizes of both the block copolymer micellar assembly and the polymeric nanogel observed by Transmission electron microscopy (TEM) are similar to those obtained by DLS. When generating composite nanostructures, it is critical that we distinctly visualize these nanostructures independently. Since both nanostructures are capable of non-covalently sequestering lipophilic guest molecules, an iodine-containing hydrophobic dye BDP-C12-I2 was incorporated in the micelles and the nanogels and was examined by TEM. As shown in FIG. 1G and FIG. 1I, these structures were indeed darker and clearer, confirming that hydrophobic guest molecules can be incorporated within the interior of these assemblies and that this feature can be used to enhance contrast in TEM.

Figure 2:
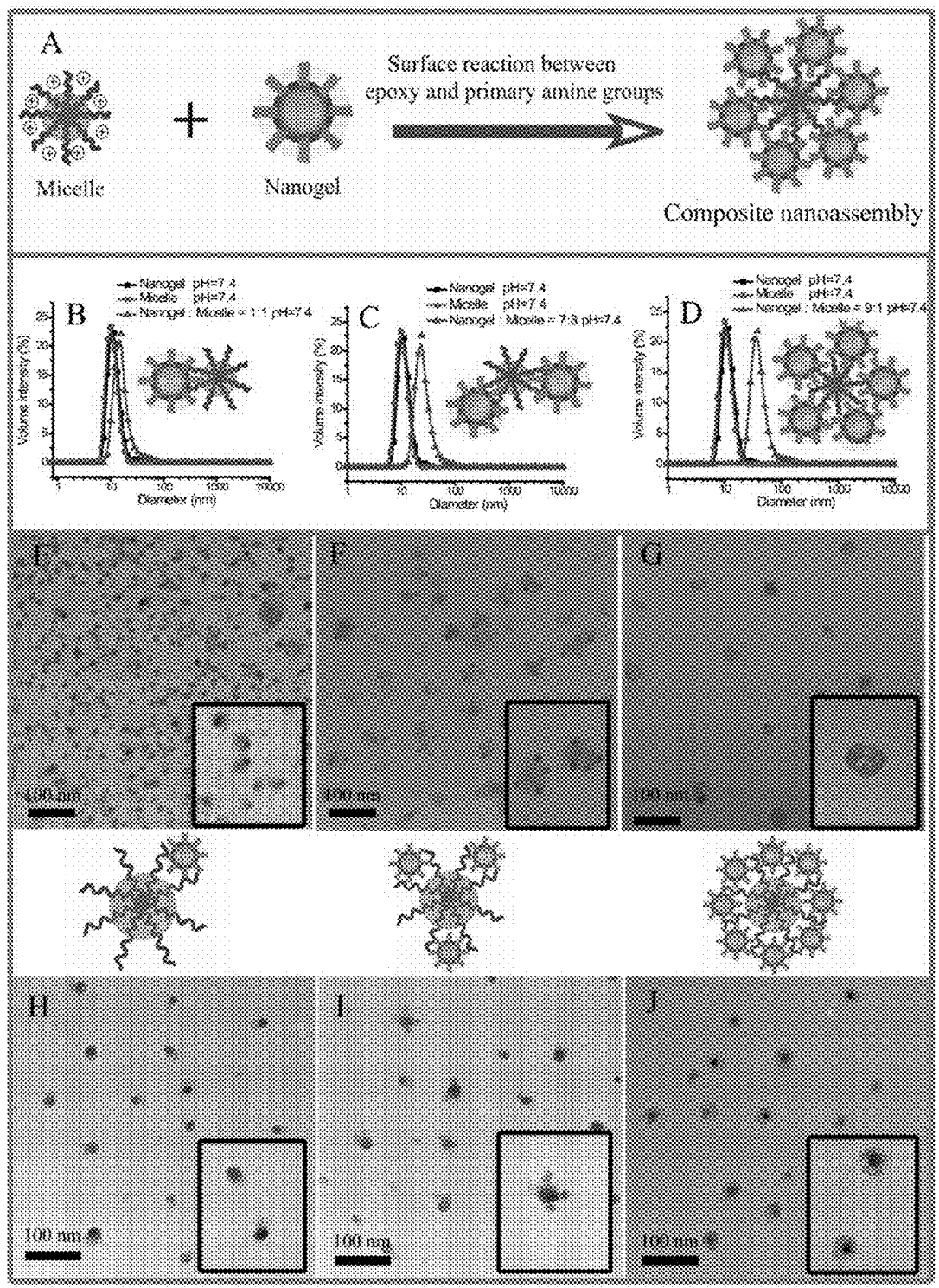
FIG. 2. (A) Schematic illustration of the construction of composite nanoassemblies from the combination of micelles and nanogels. (B), (C) and (D) give the diameter of nanogels (■), micelles (●) and the composite nanoassemblies formed from the combination of nanogels and micelles at pH=7.4 (▲). The composite nanoassemblies in (B), (C) and (D) were prepared by using nanogels and micelles with ratios 1:1, 7:3 and 9:1, respectively. The nanogels and the micelles were made from 0.5 mg/mL of random copolymer 1 and block copolymer $PDPA_{30}$-b-$PAMA_{15}$. Insets in (B), (C) and (D) illustrate the quantity change of nanogels coated on the surface of micelles. TEM images of composite nanoassemblies formed from the combination of nanogels and micelles with different ratios: (E) and (H) 1:1, (F) and (I) 7:3, (G) and (J) 9:1. For the sample preparation of (E), (F) and (G), the nanogels were loaded with BDP-C12-I2 while the micelles were empty to improve their contrast difference. For the sample preparation of (H), (I) and (J), the micelles were loaded with BDP-C12-I2 while the nanogels were empty to improve their contrast difference. The insets of all the TEM images are the magnified areas of the nanostructures. The three cartoon insets in the middle of the TEM images schematically illustrate the density of nanogels coated on the surface of micelles. The micelles and nanogels for TEM testing were formed from 2.0 mg/mL $PDPA_{30}$-b-$PAMA_{15}$ block copolymer solution and 2.0 mg/mL of random copolymer 1 solution. All scale bars in the TEM images are 100 nm.

It was discovered that composite nanoassemblies can be obtained using the combination of polymer micelles and the nanogels. The micellar assembly was expected to react with the nanogel through a reaction between the primary amine functionality present on the shell of the block copolymer assembly with the epoxide moiety present in the glycidyl methacrylate co-monomer in the nanogel. Under the reaction conditions, the amine moiety can open the epoxide ring to form the amino alcohol product. This reaction should covalently attach the polymer micellar assembly and the nanogel (FIG. 2A). The fidelity of the resultant assembly was first investigated using a 1:1 ratio of the polymer micelle and the nanogel. Although both the micelle and the nanogel independently are ~10 nm in size, the composite nanoassembly was found to be about 15 nm (FIG. 2B). When the nanogel to micelle was increased to 7:3 and 9:1, the size of the composite assembly increased to about 25 and 35 nm respectively (FIG. 2C and FIG. 2D). Composite nanoassemblies constructed from the 30 nm $PDPA_{45}$-b-$PAMA_{10}$ micelles and 10 nm nanogel (1:1 ratio) also show a clear larger size around 38 nm.

The composite assemblies were investigated by TEM. In order to distinguish the micelle from the nanogel: (a) a 25 nm micelle was used along with the 10 nm nanogel; (b) the heavy atom bearing dye molecule, BDP-C12-I2, was non-covalently incorporated into the polymer micelle or the nanogel. The results of these experiments, for the three different combinations of the micelle and nanogel, are shown in FIGS. 2E-2J. When the ratio is 1:1, most of the composite assemblies contain a 1:1 ratio of the micelle and the nanogel. This was conveniently visualized due to the presence of the guest molecule, BDP-C12-I2, as the stain. When the dye molecule was incorporated into the nanogel, a darker and smaller nanostructure is clearly fused at the shell of a lighter and larger nanostructure (FIG. 2E). On the other hand, when the guest molecule is present in the micelle, the lighter and smaller nanostructure is seen at the shell of a darker and larger nanostructure (FIG. 2H).

Statistics analysis of the TEM images, estimated from 100 composite nanoassemblies, indicates that almost 96% of composite nanoassemblies were constructed by one micelle and one nanogel. Similarly, at 7:3 ratio, a statistical distribution of the nanogels on the shell of the micelles were observed, with the average number of nanogels on the surface of the micelles corresponding to feed ratio of the micelle and the nanogel. (FIG. 2F and FIG. 2I and Table 2.) At 9:1 ratio, the micelle was completely surrounded by the nanogel, as evident from the images in FIG. 2G and FIG. 2J.

TABLE 2

Summary of $M_n$, $M_w$ and PDI of block copolymers

|  | $M_n$ | $M_w$ | PDI |
| --- | --- | --- | --- |
| PDPA$_{30}$ | 6458 | 8085 | 1.52 |
| PDPA$_{30}$-b-PAMA$_{10}$ | 8126 | 10401 | 1.64 |
| PDPA$_{30}$-b-PAMA$_{15}$ | 9036 | 11926 | 1.68 |
| PDPA$_{45}$-b-PAMA$_{10}$ | 11268 | 15099 | 1.72 |

TABLE 3

Effect of mass ratio between nanogel and micelle solution on distribution of the number of nanogels attached on micelles

| Morphologies | Mass ratio = 1:1 | Mass ratio = 7:3 |
| --- | --- | --- |
| One nanogel attached on one micelle | 96% | 11% |
| Two nanogels attached on one micelle | 3% | 24% |
| Three nanogels attached on one micelle | 1% | 32% |
| Four nanogels attached on one micelle | 0 | 27% |
| Five nanogels attached on one micelle | 0 | 6% |

Results were calculated from 100 composite nanoassemblies in TEM images.

Figure 3:
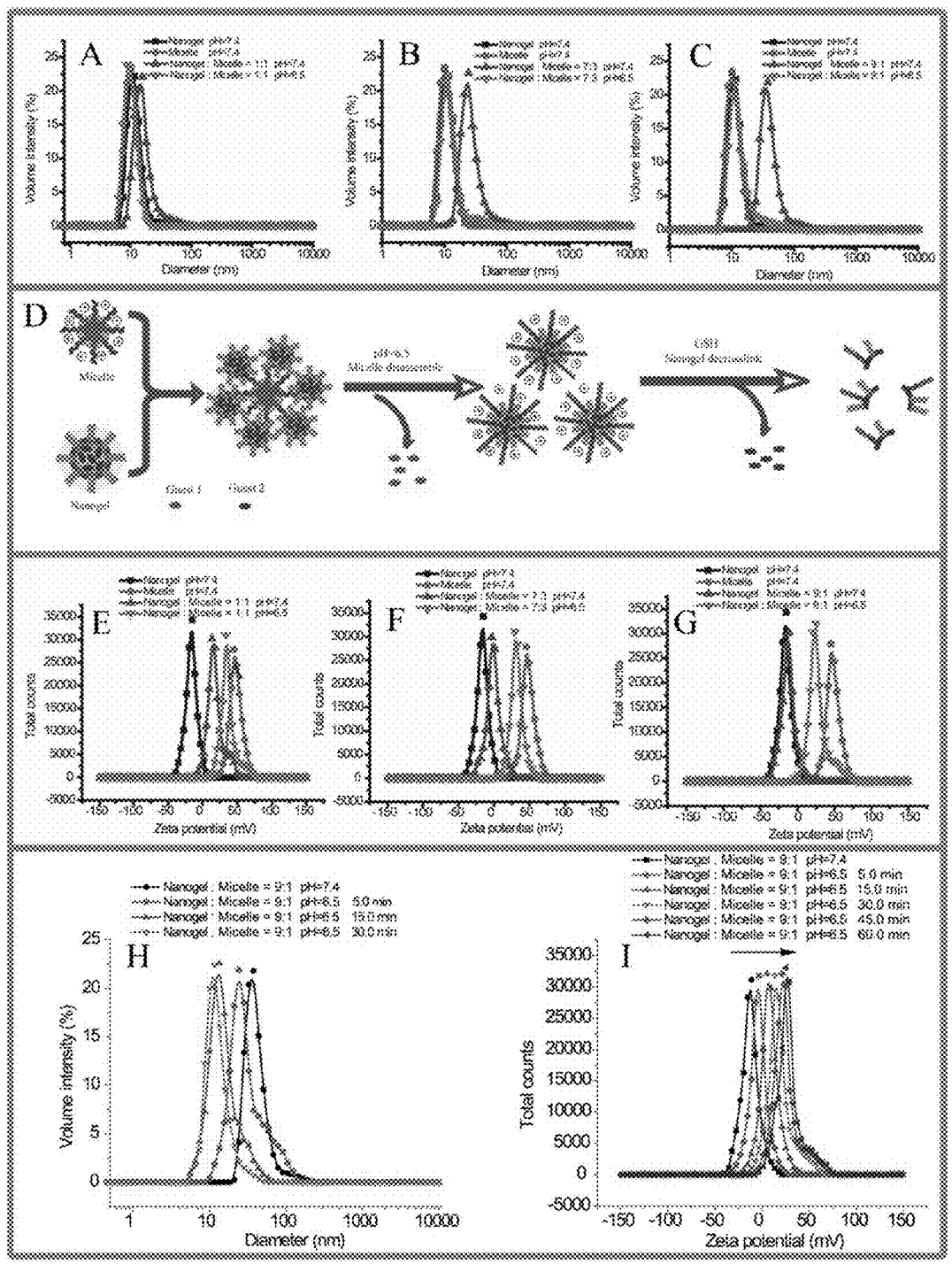
FIGS. 3(A), (B) and (C) give diameters of composite nanoassemblies in aqueous solution at pH 7.4 (▲) and 6.5 (▼). To make a comparison, diameters of nanogels (■) and micelles (●) at pH 7.4 are also illustrated. (D) Schematically illustrates the dissociation of composite nanoassemblies and the sequential release of two guests. (E), (F) and (G) show the zeta potential of nanogels (■), micelles (●) and the composite nanoassemblies at pH=7.4 (▲) and pH=6.5 (▼). The ratios between nanogels (made from 0.5 mg/mL random copolymer 1) and micelles (made from 0.5 mg/mL $PDPA_{30}$-b-$PAMA_{15}$ block copolymer) for composite nanoassemblies in (A) and (E) is 1:1, (B) and (F) is 7:3, (C) and (G) is 9:1. (H) is the disassembly kinetics of the composite nanoassemblies in aqueous solution with pH 6.5 and (I) is the zeta potential changing trend of the composite nanoassembly aqueous solution after decreasing the pH to 6.5 from 7.4. The nanogels (0.5 mg/mL) and the micelles (0.5 mg/mL) used here were made from random copolymer 1 and block copolymer $PDPA_{30}$-b-$PAMA_{15}$.

The fidelity of the individual nanoassemblies was found to remain in the composite nanoassembly. Since the block copolymer includes poly(2-(diisopropylamino) ethyl methacrylate) as the hydrophobic block, this polymer micellar assembly can be pH-sensitive. (Du, et al. 2005 *J. Am. Chem. Soc.* 127, 12800.) The p$K_a$ of the tertiary amine in this block is expected to be about 6.8. Therefore, while this amine can be unprotonated and hydrophobic at pH 7.4, a significant percentage of this amine moiety is expected to be protonated at pH 6.5. This protonation event should decrease the hydrophobicity of the block and thus diassembling the micelle. (Du, et al. 2005 *J. Am. Chem. Soc.* 127, 17982.) This was confirmed with the block copolymer micelle used in this study. Note that the composite nanoassemblies prepared from 1:1, 7:3 and 9:1 ratios of nanogels (~10 nm) and micelles (~10 nm) exhibit average diameters of about 15, 25 and 35 nm. When the pH of the solution was reduced from 7.4 to 6.5, all three composite nanoassemblies showed significant decrease in size (FIGS. 3A-3C). In fact, the final particle sizes in all these three systems at pH 6.5 were nearly the same as those of the nanogel solutions at pH 7.4, indicating that the pH-induced disassembly features of the block copolymer micelle were indeed retained in the composite assembly. We also tested this feature with the composite assemblies formed from a larger micellar assembly (~30 nm, using block copolymer PDPA$_{45}$-b-PAMA$_{10}$). Again, reduction of the pH resulted in a structure that was akin to the nanogel size at neutral pH.

The pH-induced disassembly event is schematically shown in FIG. 3D. Since the nanogel is covalently attached to the block copolymer micelle in the composite, a few polymer chains would still be attached to the nanogel after the disassembly. This feature should cause the nanogel to display the protonated tertiary amine groups at its surface, which should result in a change in the surface charge of the nanogel. The zeta potentials of the micelle and the nanogel by themselves are positive and negative, respectively. (Zhuang, et al. 2012 *ACS Macro. Lett.* 1, 175.) The surface charge of the composite nanoassemblies seemed to be understandably ratio-dependent. At 1:1 ratio, the surface charge of the composite was still positive (FIG. 3E). This is because the amount of nanogel is not enough to neutralize the positively charged micelles. The surface charge of the composite progressively moves towards that of the nanogel, as the nanogel to micelle ratio increases (FIG. 3F and FIG. 3G). When the pH is reduced from 7.4 to 6.5, the surface charge of all three composites became positive. This was also tested using the larger micellar assembly, formed from PDPA$_{45}$-b-PAMA$_{10}$, and the results were similar.

To test the correlation between the composite disassembly event and the surface charge change, the time needed to reach saturation in size change was compared with that for the change in surface charge. The 9:1 composite was used for the study, where the size change was saturated within 30 minutes upon decreasing the solution pH from 7.4 to 6.5 (FIG. 3H). On the other hand, it took about 60 min. for the zeta potential change to saturate (FIG. 3I).

Figure 4:
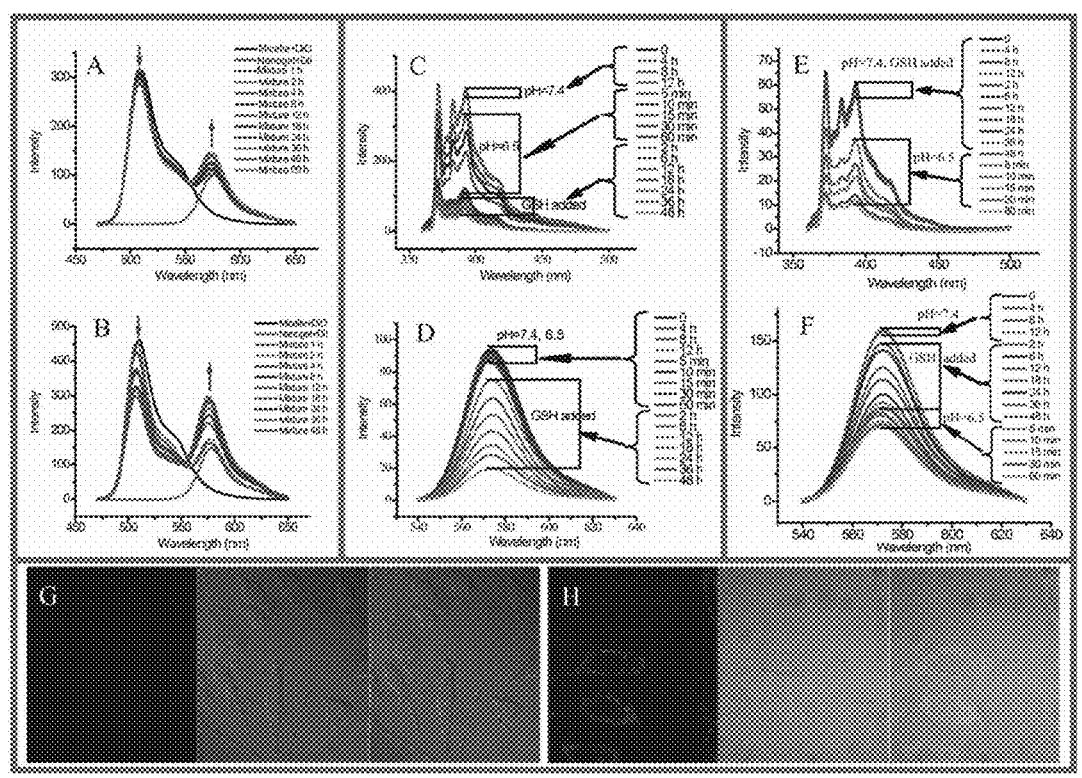
FIG. 4. FRET behavior of the composite nanoassemblies (formed from 1:1 ratio of nanogels and micelles) encapsulated with DiO and DiI, see (A) and (B). The crosslinking percentages of the as used nanogels (copolymer 1, 0.5 mg/mL) were (A) 40%, (B) 20%. Micelles used here are prepared from 0.5 mg/mL of $PDPA_{30}$-b-$PAMA_{15}$. The excitation wavelength of these two systems was 450 nm. Fluorescence spectra trace the release of pyrene and DiI from the composite nanoassemblies in response to pH and GSH. In the case of (C) and (D), the composite nanoassembly solution pH was firstly decreased from 7.4 to 6.5, and then GSH (70 mM) was added in the solution. In the case of (E) and (F) GSH (5 mM) was firstly added to uncrosslink the nanogel. Then, the pH of the solution was decreased from 7.4 to 6.5 (the reason why using 5 mM of GSH is that a high concentration of GSH could lead to a evident decrease of solution pH). The composite nanoassemblies were constructed by 9:1 ratio of copolymer 1 nanogels (0.5 mg/mL) and $PDPA_{30}$-b-$PAMA_{15}$ micelles (0.5 mg/mL). All the nanogels used in the release testing were 40% crosslinked. Pyrene was encapsulated in the micelles, while the DiI was encapsulated in nanogels. (G) and (H) are cell uptake of composite nanoassemblies at pH 7.4 and 6.5 after incubation with cells for 30 min. The composite nanoassemblies used here were made from 9:1 ratio of copolymer 1 nanogels (0.5 mg/mL) and $PDPA_{30}$-b-$PAMA_{15}$ micelles (0.5 mg/mL). Cells were imaged using a 60×water-immersion objective.

Similarly, the nanogel used in this composite assembly was sensitive to the tripeptide, glutathione (GSH). GSH can cleave disulfide bonds through a thiol-disulfide exchange reaction, which results in uncrosslinking of the nanogel (FIG. 3D). GSH-sensitive guest release was monitored to investigate whether the nanogel also preserves its salient features in the composite assembly. A fluorescence resonance energy transfer (FRET)-based method was employed to evaluate the encapsulation stability of the composite nanoassemblies, where the polymer micelle contains the FRET donor (3, 3'-dioctadecyloxacarbocyanine perchlorate (DiO)) and the nanogel contains the FRET acceptor (1,1'-dioctadecyl-3,3,3',3'-tetramethylindocarbocyanine perchlorate (DiI)). (Jiwpanich, et al. 2010 *J Am, Chem. Soc.* 132, 10683.) Under the conditions of the formation of the composite nanoassembly and in the following times, FRET efficiency was monitored. If there is a significant dye exchange from nanogel to micelle or vice versa, then there should be a FRET evolution with time. If not, there should be little or no FRET evolution. FIG. 4A and FIG. 4B show that the FRET evolution was very slow even over a 48 hour time period, compared to FRET evolutions observed in leakier micellar assemblies or nanogels reported in the literature. (Ryu, et al. 2010 *J. Am. Chem. Soc.* 132, 17227.) The composite nanoassemblies made of 40% crosslinked nanogels showed even slower FRET evolution, compared to the 20% crosslinked nanogels.

To evaluate whether the nanogel and the micellar assemblies can be independently sensitive to their respective stimuli, thus retaining their salient features, MI and pyrene were incorporated in these assemblies respectively. Since these two dye molecules exhibit absorption and emission at sufficiently different wavelengths, their release can be conveniently monitored independently. FIG. 4C and FIG. 4D show that neither pyrene nor DiI was released from the composite nanoassemblies at pH 7.4, as their emission intensities did not change with time. However, upon lowering the solution pH to 6.5, the emission intensity of pyrene decreased rapidly within 1 hr, while no change can be observed in the DiI fluorescence spectra during this period. Since pyrene was encapsulated in the micelles, this indicates micellar disassembly, consistent with DLS and zeta potential data above. Then, 70 mM GSH was added to ascertain whether the DiI, encapsulated within the nanogel, can be released. Indeed, the fluorescence intensity of the DiI decreased gradually with time (FIG. 4D). This decrease is attributable to the GSH-induced cleavage of the disulfide bonds, thus uncrosslinking the nanogels and releasing the guest molecules. This was further confirmed by monitoring the degree of DiI release, which decreased with decreasing the GSH concentration.

Figure 28:
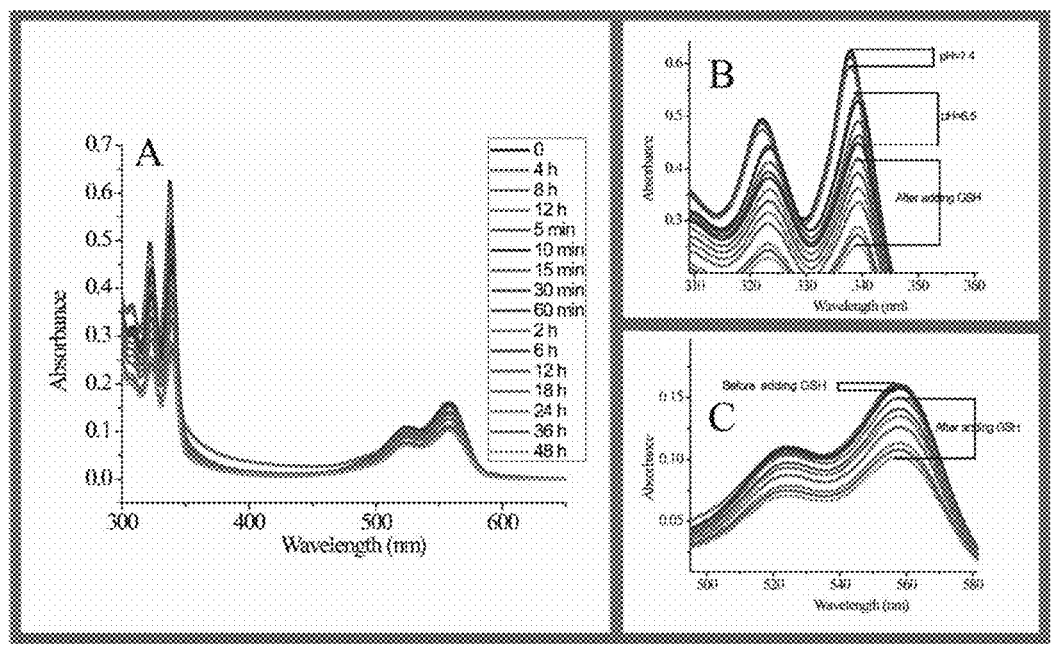
FIG. 28. UV/vis spectra running after the sequential release of pyrene and DiI from the composite nanocontainers (formed from 9:1 ratio of nanogels and micelles) (A). (B) and (C) are the magnified areas of (A). The nanogels used here are 40% crosslinked from the 0.5 mg/mL of copolymer 1, the micelles are prepared from 0.5 mg/mL of $PDPA_{30}$-b-$PAMA_{15}$ and the GSH added for the release of DiI was 0.1 mM.

In addition, also tested was the independent release of pyrene and DiI by firstly adding GSH to the system, then decreasing the solution pH from 7.4 to 6.5. The results are shown in FIG. 4E and FIG. 4F, which indicate that these two guests can be released separately. Conclusions based on fluorescence decrease can be deceiving, as this decrease could be due to extraneous factors other than release. Absorption spectrum was also measured and the results were consistent with the guest release. FIG. 4G and FIG. 4H show exemplary cell uptake at pH 7.4 and 6.5 after incubation with cells. FIG. 28 shows UV/vis spectra running after the sequential release of pyrene and DiI from the composite nanocontainers.

Thus, this disclosure demonstrated that two different polymer nanostructures, an amphiphilic block copolymer micelle and a chemically crosslinked polymeric nanogel, can be combined to form a novel composite nanoassembly. The resultant structure retains the salient features of the micelle and the nanogel independently, which has been demonstrated through their pH and redox sensitive characteristics. Using surface charge-dependent cellular uptake as the context, these composite nanostructures have also been shown to be synergistically effective. The invention is applicable to a variety of nanoscale systems and thus significantly expands the utility of the nanoscale assemblies.

Materials and Methods

Figure 5:
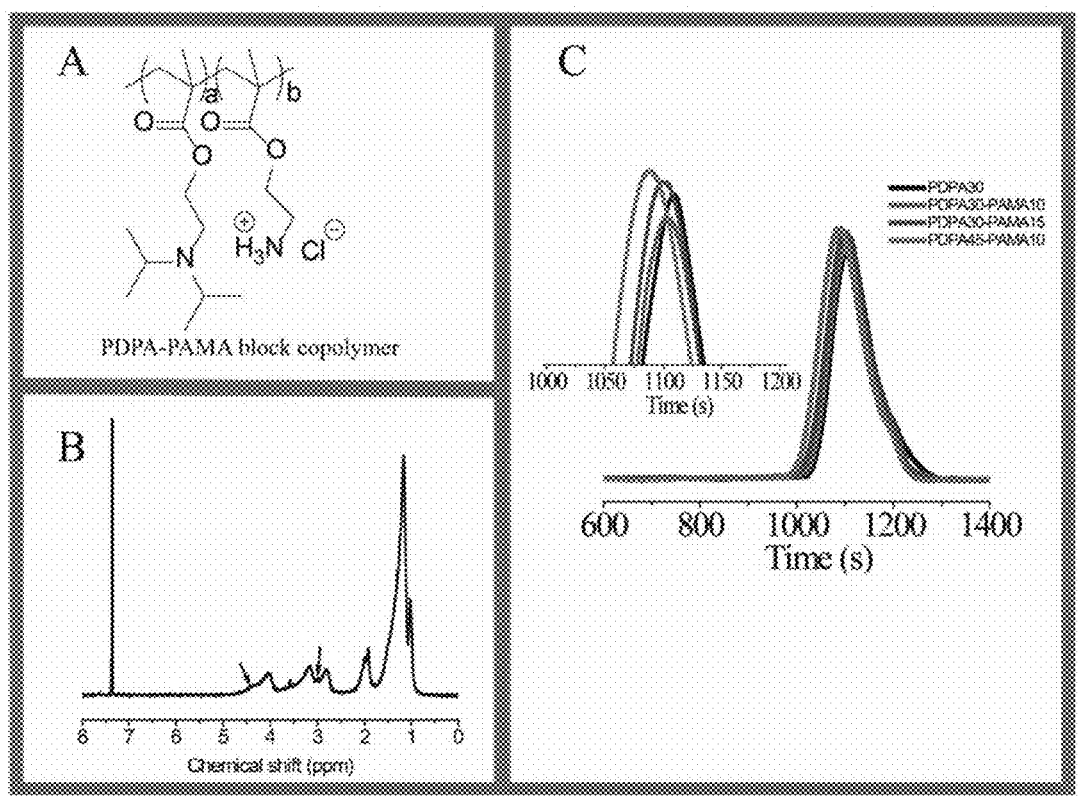
FIG. 5. Chemical structures of PDPA-b-PAMA block copolymer (A), $^1$H NMR spectrum of the $PDPA_{30}$-b-$PAMA_{15}$ block copolymer (peaks marked by the arrows represent the protons derived from the ethyl group in AMA block) (B) and aqueous GPC curves of PDPA and PDPA-b-PAMA block copolymers with different ratios of hydrophilic and hydrophobic chains (C). It is observed that the chain lengths of both PDPA and PAMA calculated from the NMR spectra correlate well with that calculated from GPC curves.
Figure 6:
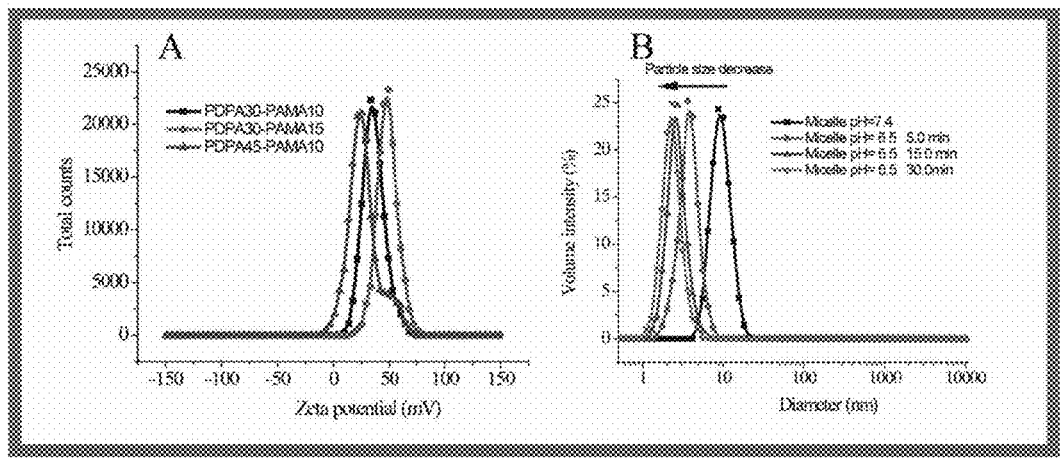
FIG. 6. Zeta potential of the micelles with 0.5 mg/mL concentration (A): pH sensitivity of the micelles (with concentration 0.5 mg/mL) formed from $PDPA_{30}$-b-$PAMA_{15}$ block copolymer (B).

Materials 2-(Diisopropylamino) ethyl methacrylate (DPA), 2-aminoethyl methacrylate hydrochloride (AMA), copper(I) bromide (CuBr), 2-propanol (IPA), 2,2'-bipyridine (bpy), pyrene, 2,2'-dithiodipyridine, 2-mercaptoethanol, polyethylene glycol monomethyl ether methacrylate (MW 450), glycidyl methacrylate (GMA), D,L-dithiothreitol (DTT), 3,3'-dioctadecyloxacarbocyanine perchlorate (DiO), 1,1'-dioctadecyl-3,3,3',3'-tetramethylindocarbocyanine perchlorate (DiI), reduced glutathione (GSH), 2,2'-azobis(2-methylpropionitrile) (AIBN), 4-cyano-4-(phenylcarbonothioylthio) pentanoic acid (chain transfer agent) and other conventional reagents were obtained from commercial sources and were used as received unless otherwise mentioned. Pyridyl disulfide ethyl methacrylate (PDSEMA) was prepared. ATRP initiator 1 (FIG. 5) was synthesized.

Synthesis of (PUPA-b-PAMA) Block Copolymer

A series of PDPA-b-PAMA block copolymers with different hydrophobic and hydrophilic chain lengths were synthesized by ATRP polymerization. A typical synthesis of $PDPA_{30}$-b-$PAMA_{15}$ follows. Catalyst CuBr (13.0 mg, 0.09 mmol), DPA (0.57 g, 2.7 mmol) and initiator 1 (30.0 mg, 0.09 mmol) were added into a 25 mL flask, which was sealed with a rubber septum. The mixture in the flask was degassed by performing three freeze-pump-thaw cycles. Then a solution of bpy (28 mg, 0.18 mmol) in 0.6 mL of IPA was degassed and injected into the flask under an argon environment. After 5 h at 50° C., the monomer conversion was higher than 95%. A degassed solution of AMA (0.225 g, 1.35 mmol) in IPA-$H_2O$ (0.36 mL-0.09 mL) was injected into the reaction mixture in argon atmosphere. After 24 h of the chain extension polymerization at 50° C., the reaction mixture was diluted with deionized water and dialysed against water (molecular weight cutoff 3500 g $mol^{-1}$) for three days to remove the catalyst and other small molecules. The block copolymer aqueous solution was freeze-dried to obtain the dry product.

Synthesis of Random Copolymer

Polyethylene glycol monomethyl ether methacrylate (1.8 g, 4.0 mmol), PDSEMA (0.76 g, 3.0 mmol). GMA (0.42 g, 3.0 mmol), 4-cyano-4-(phenylcarbonothioylthio) pentanoic acid (28 mg, 0.1 mmol) and 2,2'-azobis(2-methylpropionitrile) (5 mg, 0.03 mmol) were dissolved in 3 mL of tetrahydrofuran. The mixture was poured into a 25 mL flask sealed with a rubber septum. Three freeze-pump-thaw cycles were performed to eliminate the oxygen in the mixture. After a 4 h polymerization at 70° C. argon atmosphere, the resultant mixture was dissolved in dichloromethane (5 ml) and precipitated in hexane (200 ml) three times to yield purified copolymer. To obtain copolymer with higher molecular weight, 8 h polymerization time was also used.

Preparation of Micelles

Block copolymers such as $PDPA_{30}$-b-$PAMA_{10}$, $PDPA_{30}$-b-$PAMA_{15}$ and $PDPA_{45}$-b-$PAMA_{10}$ were first dissolved in acetone to make solutions with 10 mg/mL concentration. Then the acetone solutions containing the block copolymers were injected into 10 mL of deionized water (with pH around 7.4). The obtained mixtures were left undisturbed at room temperature for 3 days to evaporate the acetone completely. To make micellar assemblies at different concentrations, 0.25, 0.5, 1.0 and 2.0 mL of copolymer acetone solutions were also used.

Preparation of Nanogels

In a typical preparation of 40 mol % crosslinked nanogel aqueous solution, 0.5 mL of random copolymer acetone solution (10 mg/mL) solution was injected into 10 mL of deionized water (with pH around 7.4). The obtained mixtures were left undisturbed at room temperature for 3 days to evaporate the acetone completely. DTT (0.15 mg, 0.001 mmol, 20 mol % against PDS groups) was added to crosslink the polymer into nanogel. Unreacted DTT and byproduct pyridothione were removed from the solution by ultrafiltration using a membrane with a molecular weight cutoff of 3,500 g $mol^{-1}$. To prepare 20 mol % crosslinked nanogel, 0.075 mg of DTT was added. Different volumes of random copolymer acetone solution such as 0.25, 1.0 and 2.0 mL were also used to make nanogels with different concentrations.

Encapsulation of Dyes in Micelles and Nanogels

For the preparation of micelles and nanogels encapsulated with dyes (such as DiI, DiO and pyrene), dye acetone solutions (10 mg/mL) were added when injecting block copolymer or random copolymer into deionized water. Other procedures were the same with the preparation of micelle or nanogel aqueous solutions. Excess insoluble dyes were removed by filtration. The dosage of dye used here were about 10 wt % of the polymer.

Composite Nanoassemblies from the Combination of Micelles and Nanogels

The combination between micelles and nanogels was realized by the surface reaction of amino and epoxy groups, because this reaction can take place in neutral aqueous solution. A typical combination of micelles with nanogels (mass ratio=1:1) was as follows. 0.5 mL of PDPA$_{30}$-b-PAMA$_{10}$ block copolymer micelle aqueous solution (0.5 mg/mL) and 0.5 mL of crosslinked nanogel (prepared using random copolymer from 6.0 h polymerization) aqueous solution (0.5 mg/mL) were mixed together. The mixture was left undisturbed overnight, to let the micelles combine with nanogels completely. To control the final morphology and property of the composite nanoassemblies, various mass ratios of micelle and nanogel such as 3:7 and 1:9, and different concentrations of micelle and nanogel solutions were also adopted. Micelles and nanogels encapsulated with different dyes (such as DiI, DiO and pyrene) were also used to make composite nanoassemblies loaded with guest molecules.

Characterization $^1$H-NMR spectra were recorded on a 400 MHz Bruker NMR spectrometer with 1000 scans at a relaxation time of 2 s. Molecular weights of the random copolymers were estimated by gel permeation chromatography (GPC) with a refractive index detector using THF as eluent (PMMA was used as standard). Molecular weights of PDPA-b-PAMA block copolymers were measured by aqueous GPC at 35° C. using poly(2-vinyl pyridine) as standard. The eluent was a buffer solution containing 0.30 M NaH$_2$PO$_4$ and 1.0 M acetic acid (the pH is 3.3). Dynamic light scattering (DLS) and zeta potential measurements were performed using a Malvern Nanozetasizer. The fluorescence spectra were obtained from a JASCO FP-6500 spectrofluorimeter. UV/Vis spectra of the samples in aqueous solutions were measured on a Unico UV/Vis 2802PCS instrument. Transmission electron microscopy (TEM) images were taken from JEOL 100CX at 100 KV.

Sequential Release of Different Dyes from Composite Nanoassemblies

Composite nanoassemblies with pyrene encapsulated in micelles and DiI encapsulated in nanogels were used to evaluate the sequential release of different dyes under different stimuli. The composite nanoassemblies loaded with dyes were first made in deionized water at pH around 7.4. Then HCl aqueous solution (0.01 mol/L) was used to adjust the solution of composite nanoassemblies to 6.5. The fluorescence spectra of the mixture were recorded at regular intervals to monitor the dye release progress. After the release of dyes reached its equilibrium, GSH was added to the mixture. The fluorescence spectra of the mixture were also recorded at regular intervals. UV/Vis spectra were also recorded to trace the release progress after the changing of pH and the addition of GSH. In contrary, we also tested the sequential release of dyes by firstly adding GSH to the composite nanoassembly solution, and then decreasing the pH of the solution from 7.4 to 6.5.

Figure 14:
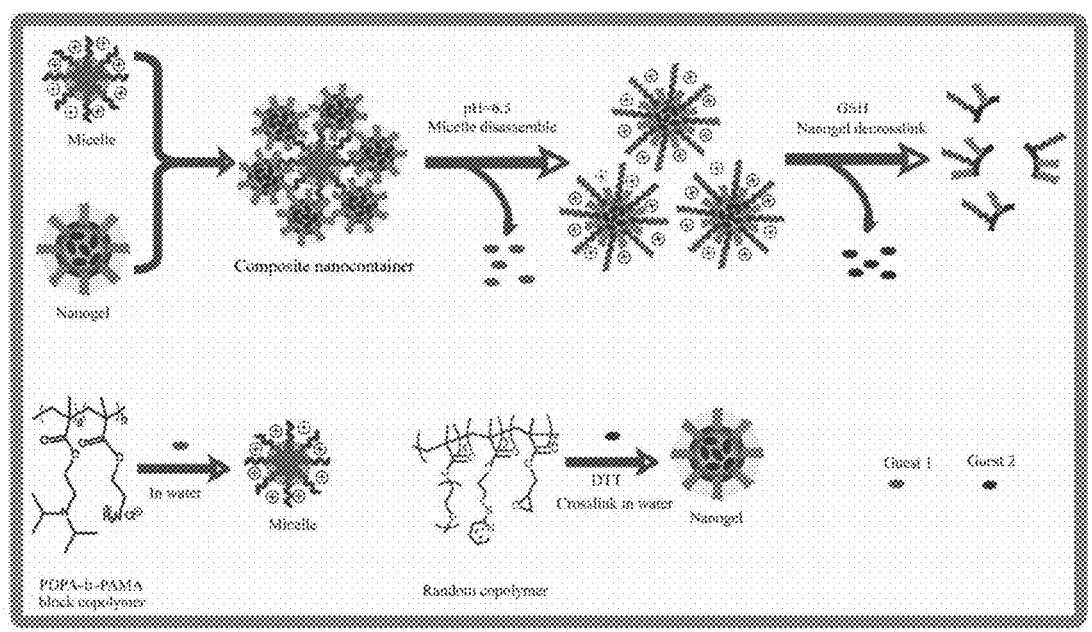
FIG. 14. Schematic illustration of the construction and dissociation of composite nanocontainers from the combination of micelles and nanogels. The chemical link between micelles and nanogels are formed by the reaction between amino groups on the block copolymer and epoxy groups on the random copolymer. Disassembly of the micelles at pH 6.5 can liberate nanogels, change their surface charge and release the guest 1. Uncrosslinking of the nanogels by GSH results in the release of guest 2. DTT in the scheme is D,L-dithreitol.

Example II. Nano-Vehicles for Controlled, Targeted and Sequential Delivery of Two Agents The intelligent composite nanocontainers of the invention, made from the combination of nanogels and micelles, allow simultaneously achieve triggered, targeted and sequential delivery of guests (FIG. 14). As shown herein, the micelles can be designed to be positively charged and disassemble at pH around 6.5, which corresponds to that in tumor cell environment. The nanogels can be designed to be redox sensitive and can be decrosslinked when encountering the reduced glutathione (GSH), which is intracellularly overexpressed in tumor cell. It is a common view that both normal cells and tumor cells can absorb the positively charged nanoparticles fast and thereby resulting in an non-specific cell uptake.

For example, the micelles may be coated with neutral (or slightly negatively charged) nanogels via surface chemical reaction to shield their positive charges. When encountering weak acid target sites (such as tumor cell tissues with pH around 6.5), the disassembly of the micelles would lead to the liberation of nanogel. At the same time, the positively charged block copolymer would attach to the nanogel surface, causing the charge change of the nanogel from neutral (or slightly negative) to positive. Subsequently, the positively charged nanogel will be easily internalized by the cells in the target sites.

Significant features of this delivery system include: (I) the positive charges are properly shielded and opportunely exposed after the composite nanocontainers reach the target sites, which would lead to a highly specific cell uptake: and (2) both the micelles and nanogels used here are sensitive to different stimuli, making it possible to release two different guest molecules sequentially in exterior and interior of the cells.

Morphology of the Composite Nanocontainers

Figure 21:
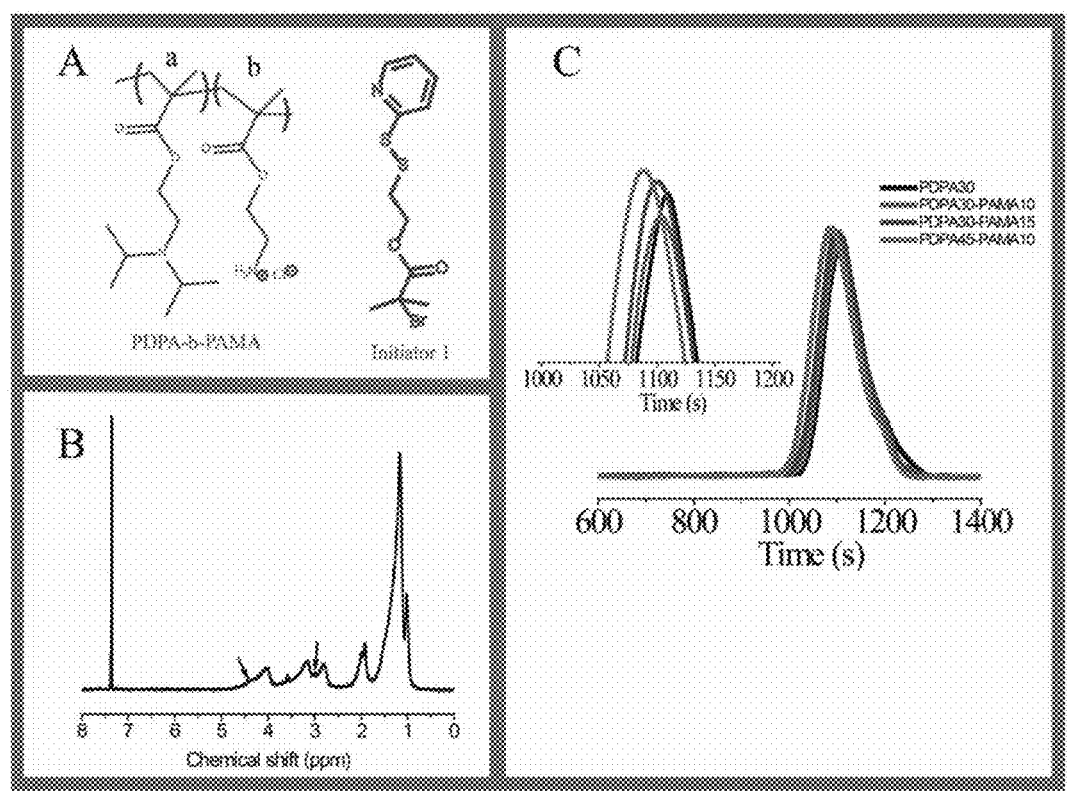
FIG. 21. Chemical structures of PDPA-b-PAMA block copolymer and ATRP initiator (A), $^1$H NMR spectrum of the $PDPA_{30}$-b-$PAMA_{15}$ block copolymer (peaks marked by the arrows represent the protons derived from the ethyl group in AMA block) (B) and aqueous GPC curves of PDPA and PDPA-b-PAMA block copolymers with different ratios of hydrophilic and hydrophobic chains (C). It is observed that the chain lengths of both PDPA and PAMA calculated from the $^1$H NMR spectra accord well with that calculated from GPC curves.

The micelles were formed from the self-assembly of poly((2-(diisopropylamino) ethyl methacrylate-b-2-amino-ethyl methacrylate hydrochloride) (PDPA-b-PAMA) block copolymer which was synthesized by atom transfer radical polymerization (ATRP) (FIG. 21 and Table 4).

TABLE 4

Summary of $M_n$, $M_w$ and PDI of the PDPA and PDPA-b-PAMA block copolymers

| | $M_n$ | $M_w$ | PDI |
|---|---|---|---|
| PDPA$_{30}$ | 6458 | 8085 | 1.52 |
| PDPA$_{30}$-b-PAMA$_{10}$ | 8126 | 10401 | 1.64 |
| PDPA$_{30}$-b-PAMA$_{15}$ | 9036 | 11926 | 1.68 |
| PDPA$_{45}$-b-PAMA$_{10}$ | 11268 | 15099 | 1.72 |

Figure 22:
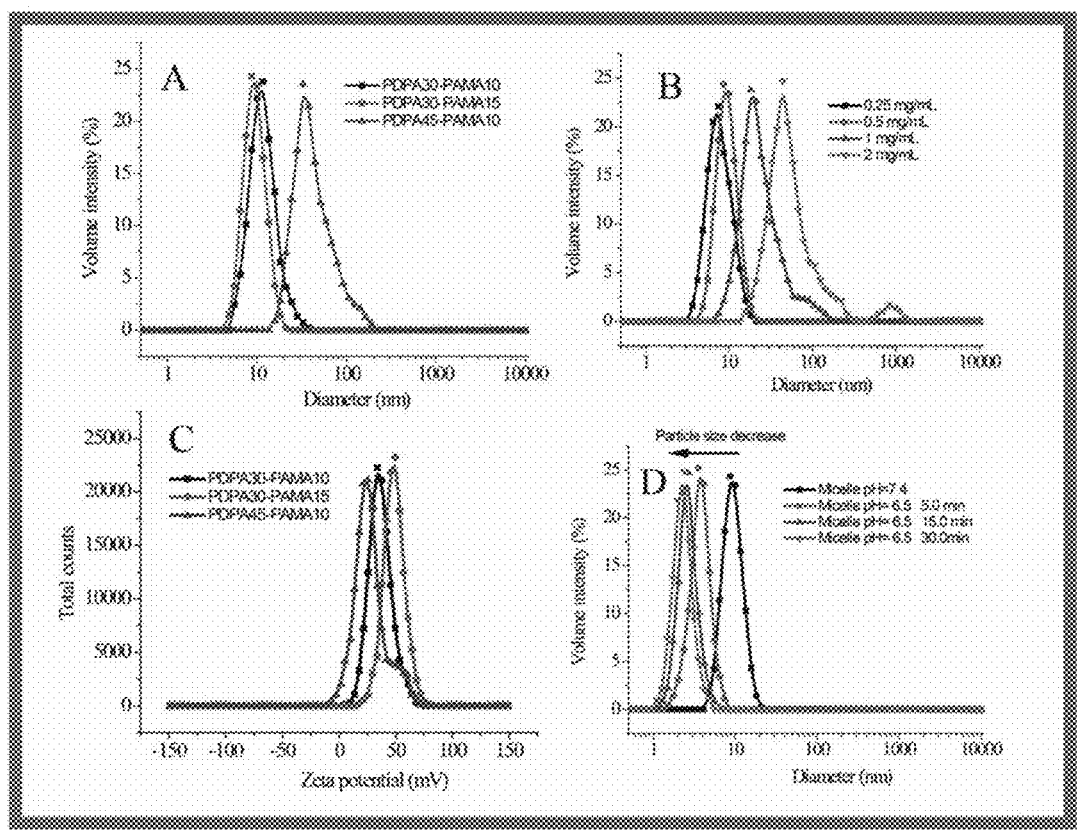
FIG. 22. The diameters of micelles (with concentration 0.5 mg/mL) formed from PDPA-b-PAMA block copolymer with different ratios of hydrophobic and hydrophilic chain lengths (A): effect of concentration on the diameter of micelles prepared from $PDPA_{30}$-b-$PAMA_{15}$ block copolymer (B); zeta potential of the micelles with 0.5 mg/mL concentration (C); pH sensitivity of the micelles (with concentration 0.5 mg/mL) formed from $PDPA_{30}$-b-$PAMA_{15}$ block copolymer (D).
Figure 23:
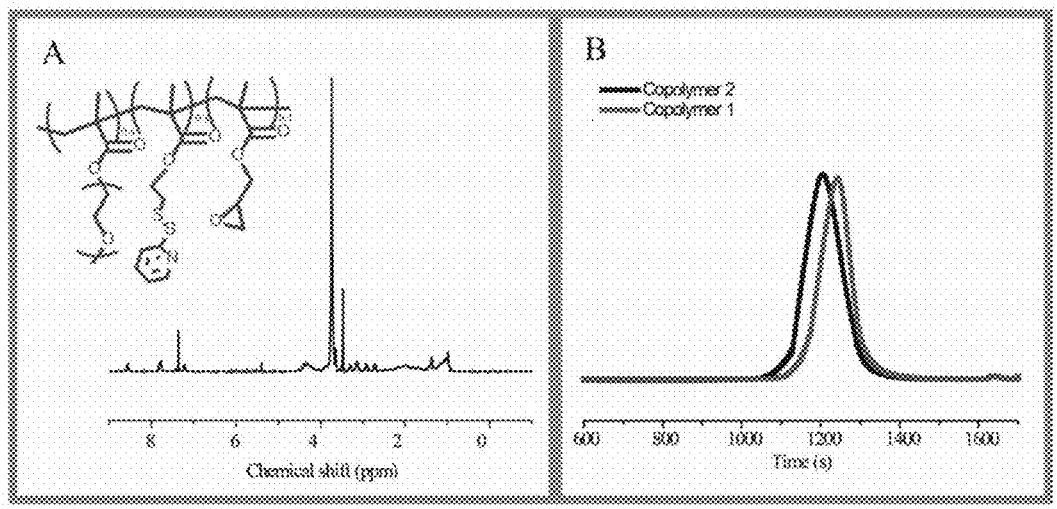
FIG. 23. Chemical structure of random copolymers and $^1$H NMR spectrum of the random copolymer (A) and THF GPC curves of random copolymers synthesized from 4 and 8 h polymerization time (B).

Dynamic light scattering (DLS) results shown in FIGS. 22A and B indicate that the diameter of the micelles can be controlled by both the polymer concentration and the ratio of hydrophilic and hydrophobic segments. The surface of the micelles is positively charged (FIG. 22C) because the amino groups on the hydrophilic segments are protonated. The micelles exhibit a fast response to the change in pH, because the tertiary amine groups on PDPA chains can be protonated in weakly acidic solutions. After decreasing the pH from 7.4 to 6.5, the micelles disassembled completely in 30 min (FIG. 22D). The nanogels were prepared from the crosslinking of random copolymer poly(polyethylene glycol monomethyl ether methacrylate-co-glycidyl methacrylate-co-pyridyl disulfide ethyl methacrylate) (P(EGMA-GMA-PDSEMA)) by the formation of disulfide bonds using DTT (FIG. 23 and Table 5).

TABLE 5

Summary of $M_n$, $M_w$ and PDI of the random copolymers for nanogels

| | $M^n$ | $M_w$ | PDI |
|---|---|---|---|
| Copolymer 1 | 21044 | 26691 | 1.26 |
| Copolymer 2 | 25464 | 35558 | 1.38 |

Figure 24:
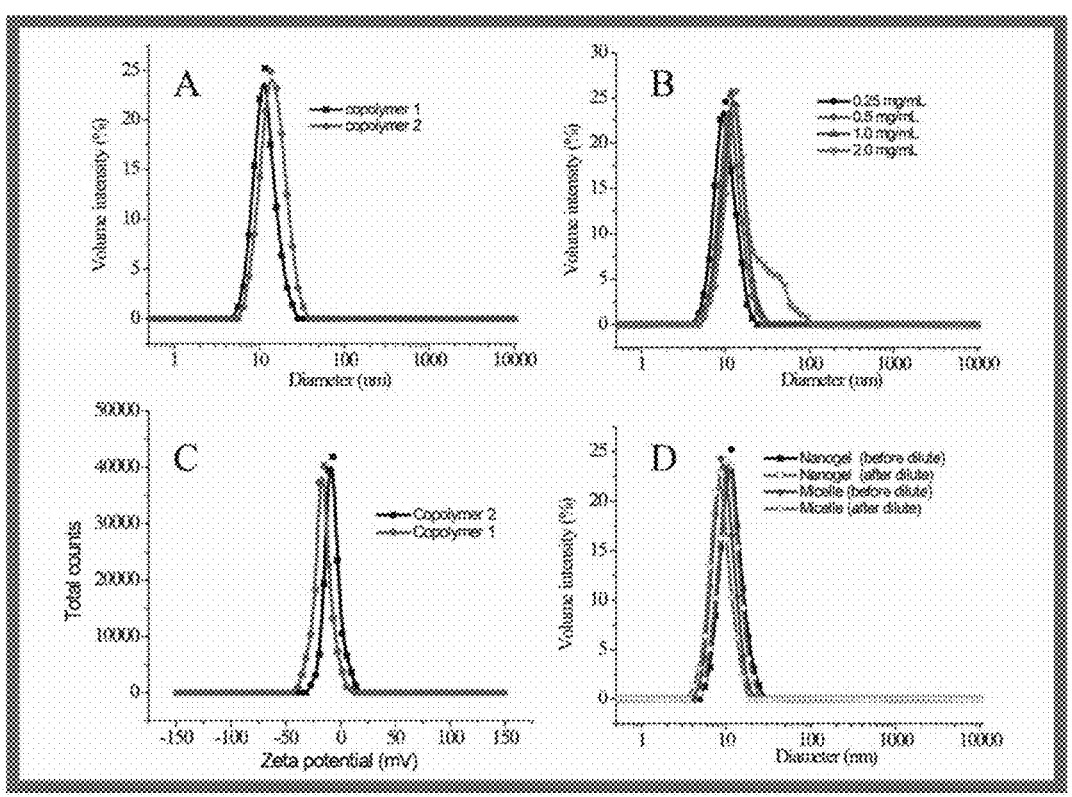
FIG. 24. Diameter of the nanogels (0.5 mg/mL) formed from random copolymers with different molecular weight (A); effect of concentration on the diameter of micelles prepared from random copolymer 1 (B); zeta potential of nanogels with 0.5 mg/mL concentration (C); diameter of the nanogels (formed from random copolymer 1) and micelles (formed from $PDPA_{30}$-b-$PAMA_{15}$) with 0.5 mg/mL concentration before and after diluting to double volume (D). The nanogels used in these testing were 40% crosslinked.

Previous investigations have confirmed that these nanogels are redox sensitive, because their crosslinked network can be cleaved when encountering GSH. (Ryu, et al. 2010 *J. Am. Chem. Soc.* 132, 17227-17235; Ryu, et al. 2010 *J. Am. Chem. Soc.* 132, 8246-8247.) DLS measurements show that the diameter of the nanogels is around 10 nm, and increases slightly with the increasing of polymer molecular weight, but depends less on the polymer concentration (FIGS. 24A and B). The surface of the nanogels is negatively charged (FIG. 24C) which may be induced by the carboxyl group on the chain transfer agent used in the synthesis of P(EGMA-GMA-PDSEMA) random copolymer. We also evaluated the stability of the micelles and nanogels upon dilution. The results shown in FIG. 24D indicate that the diameters of both micelles and nanogels change little after the dilution of the solution, which suggests that they are stable in water.

Figure 15:
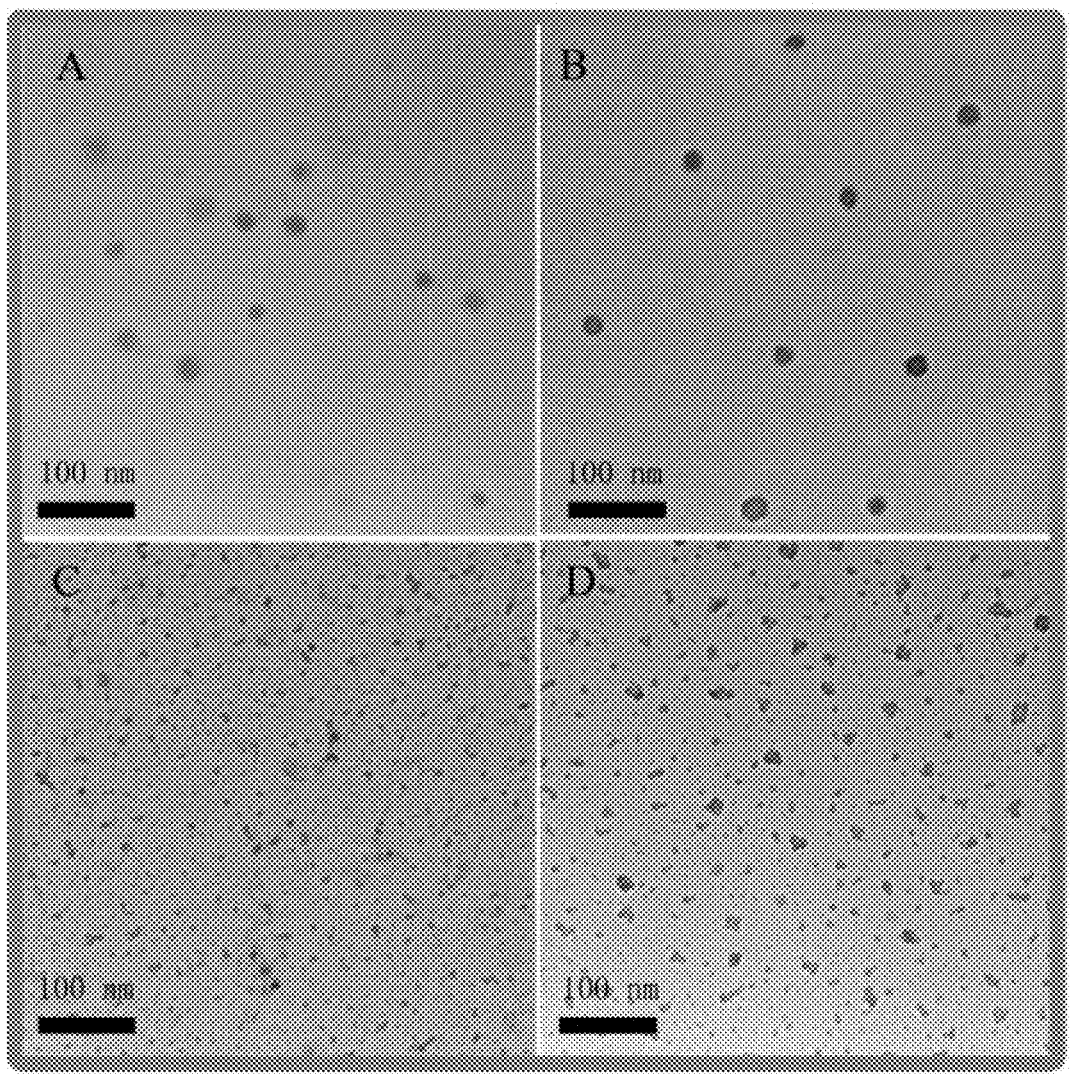
FIG. 15. TEM images of micelles before (A) and after (B) encapsulation of BDP-C12-I2; and nanogels before (C) and after (D) encapsulation of BDP-C12-I2. The aim of loading BDP-C12-I2 in the micelles and nanogels is to increase their contrast in the TEM testing. The micelles were formed from 2.0 mg/mL of $PDPA_{30}$-b-$PAMA_{15}$ block copolymer solution, while the nanogels were prepared by 2.0 mg/mL of random copolymer 1 solution.
Figure 25:
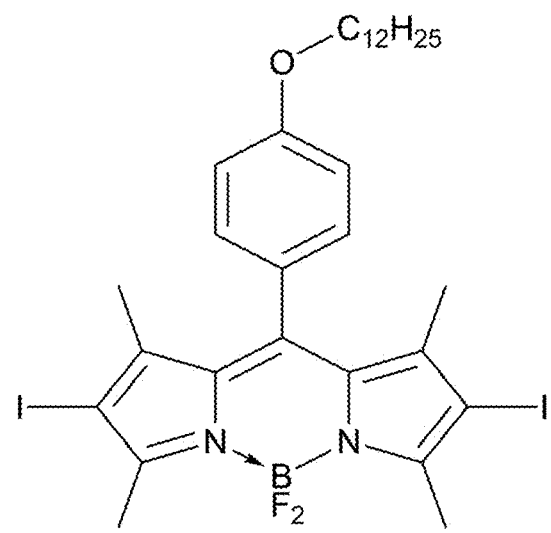
FIG. 25. Chemical structure of BDP-C12-I2.

A hydrophobic dye, BDP-C12-I2 (FIG. 25) was encapsulated, which contains iodine atoms, in the nanogels or micelles to increase their contrast in TEM images. To further identify the micelles from the nanogels, we chose the micelles formed from 2 mg/mL block copolymer solution for the TEM analyses, because they have distinctly larger diameters (FIG. 22B). The TEM images shown in FIG. 15 reveal that the micelles have average diameter about 25 nm, while the nanogels have average diameter around 5 nm. After loading the micelles or nanogels with BDP-C12-I12, it is observed that the nanoparticles become darker and clearer. This result confirms that encapsulating BDP-C12-I2 in these nanoparticles can evidently increase their contrast.

To study the morphology of the composite nanocontainers obtained from the combination of micelles and nanogels, first used were the nanogels loaded with BDP-C12-12 to combine with empty micelles. FIG. 16A shows the TEM image of the composite nanocontainers prepared using 1:1 ratio of nanogels and micelles. It is clear that each "dark" spot is attached to one bigger "lighter" spot. The dark spots are indeed nanogel, and the light spots are micelles. TEM image of the composite nanocontainers with a higher nanogel-to-micelle ratio (7:3) showed that every micelle is decorated by several nanogels (FIG. 16B).

Figure 16:
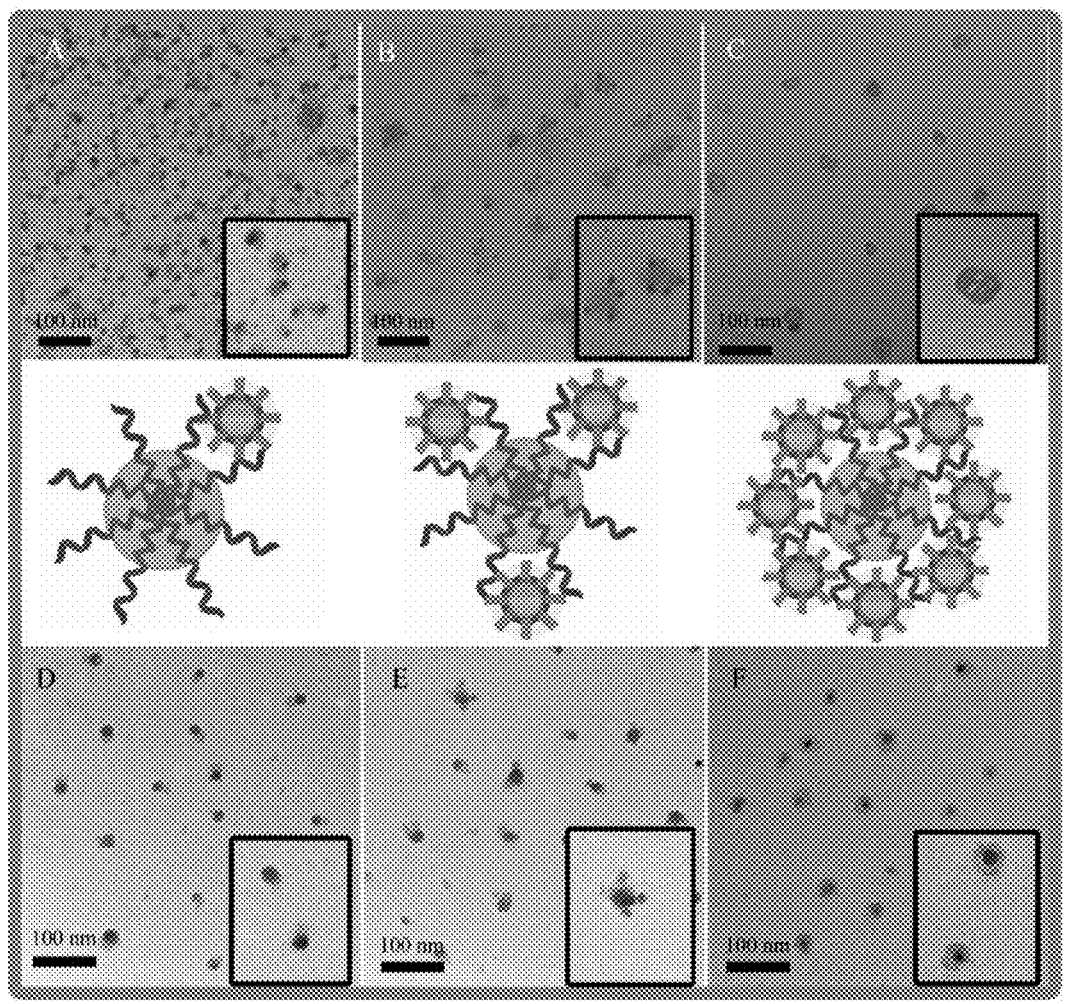
FIG. 16. TEM images of composite nanocontainers formed from the combination of nanogels and micelles. The ratio of nanogels and micelles in (A) and (D) is 1:1, in (B) and (E) is 7:3 while in (C) and (F) is 9:1. For the sample preparation of (A), (B) and (C), the nanogels were loaded with BDP-C12-I2 while the micelles were empty to improve their contrast difference. For the sample preparation of (D), (E) and (F), the micelles were loaded with BDP-C12-I2 while the nanogels were empty to improve their contrast difference. The insets of all the TEM images are the magnified areas of the nanostructures. The three cartoon insets in the middle of the TEM images schematically illustrate the density of nanogels coated on the surface of micelles. The micelles were formed from 2.0 mg/mL $PDPA_{30}$-b-$PAMA_{15}$ block copolymer solution, and the nanogels were prepared by 2.0 mg/mL of random copolymer 1 solution.

Furthermore, it was found that the composite nanocontainers prepared by using 9:1 ratio of nanogels and micelles exhibit a "hollow" core with a darker corona (FIG. 16C). At this high ratio, the nanogels coat the surface of micelles densely enough that leads to the formation of dark shells. Concurrently, the low contrast of the micelles implies that the composite nanocontainers show core-shell type morphology. The statistical density of the nanogels attached to the micelle surface can be reproducibly and easily controlled by merely altering the ratio of nanogels to micelles (as shown in the three cartoon insets in FIG. 16).

Figure 26:
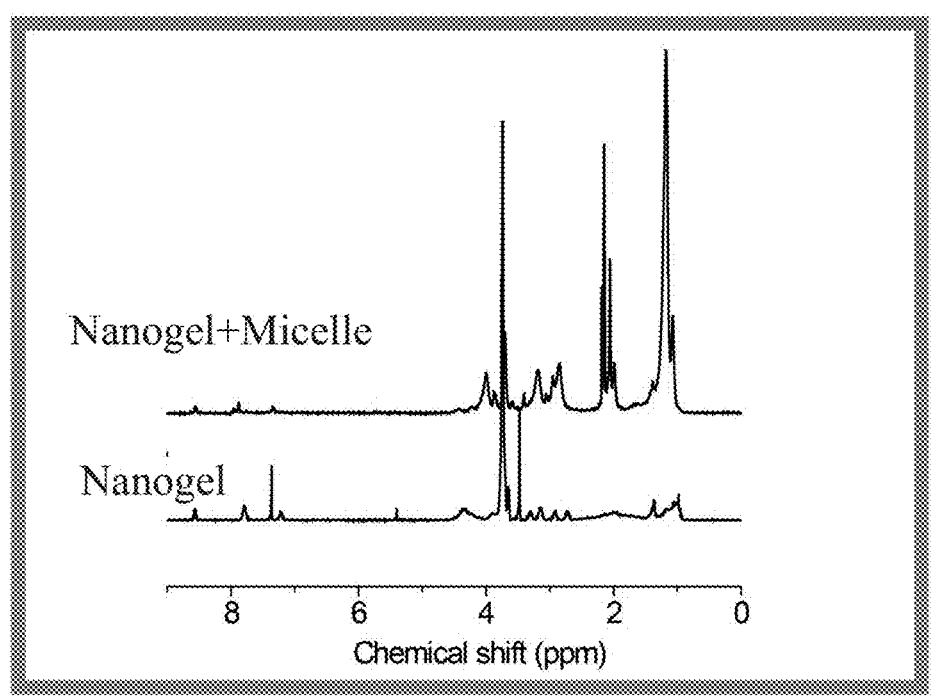
FIG. 26. $^1$H NMR spectra of the nanogels and the composite nanocontainers obtained from nanogels and micelles (the ratio is 1:1) in $CDCl_3$.

The micelles were loaded with BDP-C12-I2 to improve their contrast. FIGS. 16D-F and their insets give the morphologies of the composite nanocontainers prepared by 1:1, 7:3 and 9:1 ratios of nanogels and micelles, respectively. The micelles with larger size become darker, but the nanogels with smaller size are lighter. The density of the nanogels coated on the surface of micelles increases with the increasing of the ratio, which accords well with the result shown in FIG. 16A-C. Especially in the case of 9:1 ratio, it is evident that the large density of nanogels surrounding each micelle imparts the composite nanocontainers with a darker core and a lighter corona. $^1$H NMR spectra shown in FIG. 26 indicates that the composite nanocontainers have no proton signal from the epoxy group.

Dissociation of the Composite Nanocontainers

Figure 17:
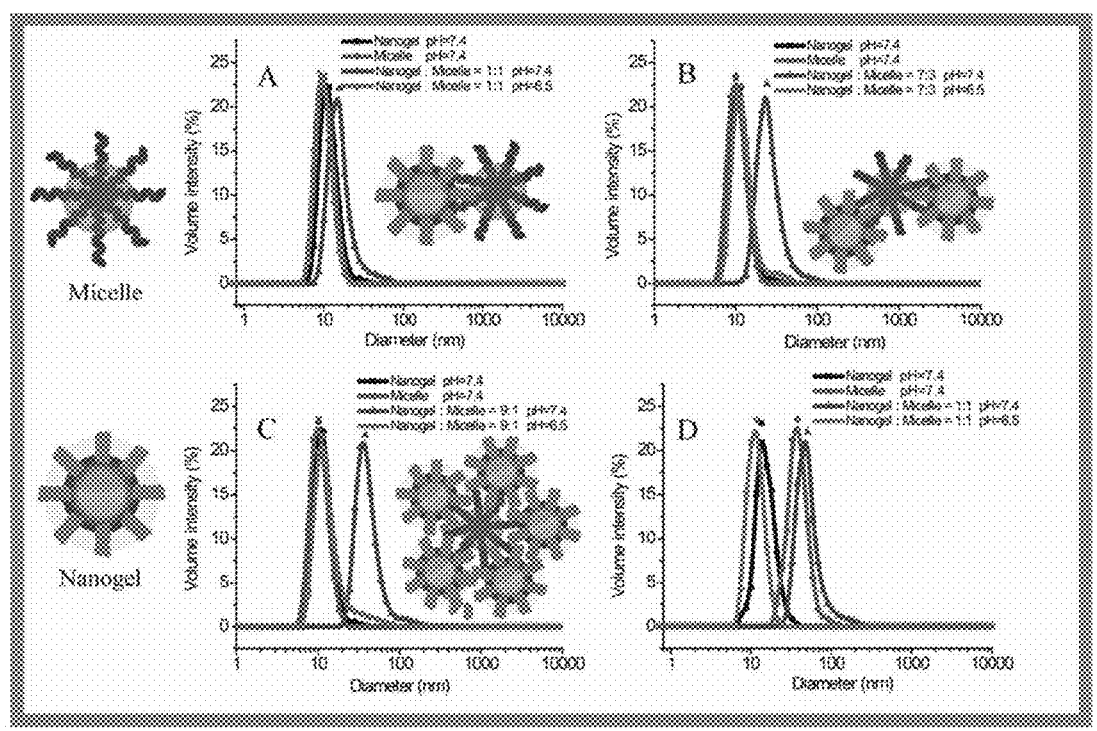
FIG. 17. Diameters of nanogels (■), micelles (●) and the composite nanocontainers formed from the combination of nanogels and micelles at pH=7.4 (▲) and pH=6.5 (▼). The composite nanocontainers in (A), (B) and (C) were prepared by using nanogels and micelles with ratios 1:1, 7:3 and 9:1, respectively. The nanogels and the micelles used in (A), (B) and (C) were made from random copolymer 1 and block copolymer $PDPA_{30}$-b-$PAMA_{15}$. While the nanogels and the micelles (with 1:1 ratio) used in (D) were prepared by copolymer 2 and block copolymer $PDPA_{45}$-b-$PAMA_{10}$. The insets in (A), (B) and (C) illustrate the quantity change of nanogels coated on the surface of micelles.

DLS measurements were also used to estimate the particle size of nanogels and micelles in aqueous solution, and trace the changes in particle size of the composite nanocontainers under different pH conditions (the results are shown in FIG. 17). Both the nanogels and micelles made from copolymer 1 and block copolymer PDPA$_{30}$-b-PAMA$_{15}$ with 0.5 mg/mL concentration possess an average particle size around 10 nm. After mixing the aqueous solution of nanogels and micelles with the same concentration, the diameter of the system increased evidently, indicating the formation of composite nanocontainers. The composite nanocontainers prepared from 1:1, 7:3 and 9:1 ratios of nanogels and micelles have average diameters about 15, 25 and 35 nm (FIG. 17A-C), which reveal that the density of the nanogels coated on the surface of the micelles increases with the increasing of nanogel-to-micelle ratio (FIG. 17A-C, insets). The pH of the mixtures was then reduced from 7.4 to 6.5 to test the pH sensitivity of composite nanocontainers. It is interesting that all the mixtures regardless of the ratio of nanogels and micelles, show significant decrease in average diameter. The final particle sizes tested from all these three systems at pH 6.5 are almost the same as that of the nanogel solutions at pH 7.4. This means that the composite nanocontainers dissociate into nanogels upon encountering a weakly acidic environment, because of the disassembly of the micelles. The nanogels formed from random copolymer 2 and micelles formed from block copolymer PDPA$_{45}$-b-PAMA$_{10}$ were used to prepare composite nanocontainers. As shown in FIG. 17D, these nanogels were also liberated from the micelles after changing the pH from 7.4 to 6.5.

Figure 18:
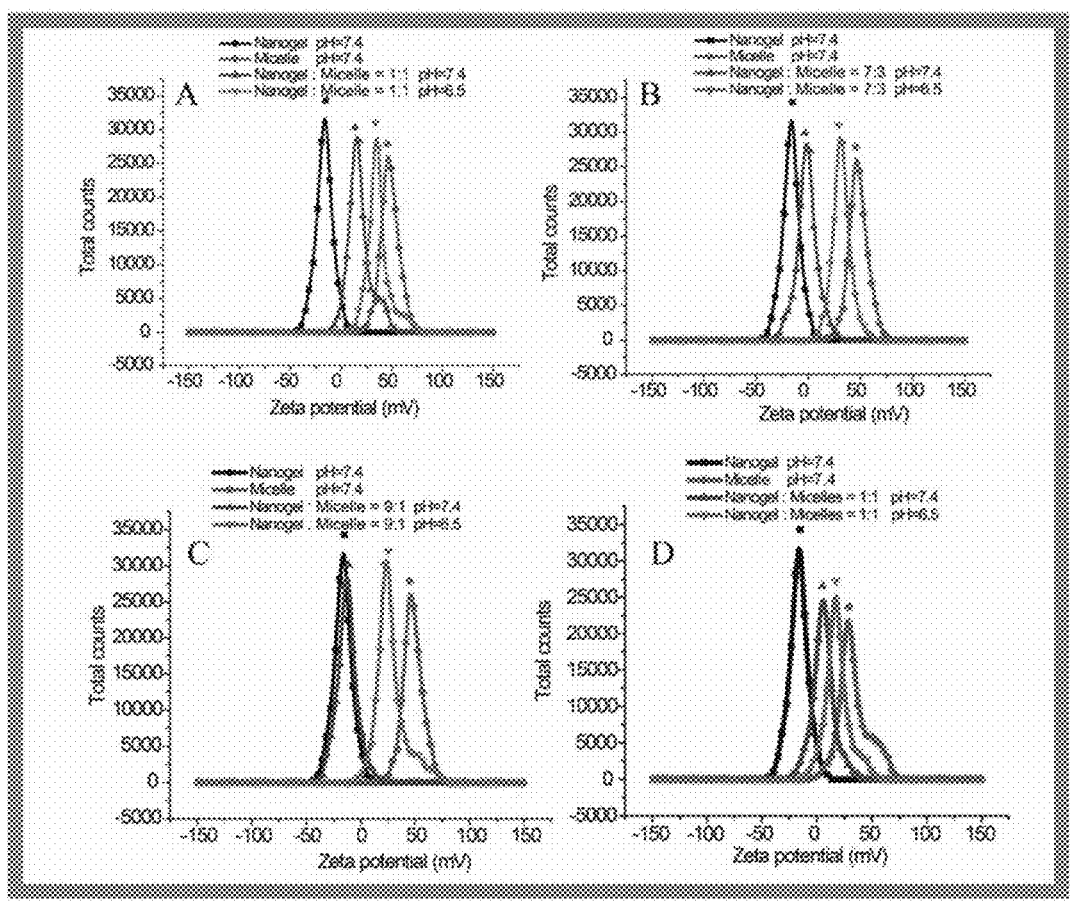
FIG. 18. Zeta potential of nanogels (■), micelles (●) and the composite nanocontainers formed from the combination of nanogels and micelles at pH=7.4 (▲) and pH=6.5 (▼). The composite nanocontainers in (A), (B) and (C) were prepared by using nanogels and micelles with ratios of 1:1, 7:3 and 9:1, respectively. The nanogels and the micelles used in (A), (B) and (C) were made from random copolymer 1 and block copolymer $PDPA_{30}$-b-$PAMA_{15}$. While the nanogels and the micelles (with 1:1 ratio) used in (D) were prepared by copolymer 2 and block copolymer $PDPA_{45}$-b-$PAMA_{10}$.

An important objective of the design is to reverse the surface charge of the nanogels via the dissociation of composite nanocontainers. The zeta potential results shown in FIG. 18A-C indicate that the nanogels (made from copolymer 1) are slightly negatively charged, but the micelles (formed by PDPA$_{30}$-b-PAMA$_{15}$) are strongly positively charged. After mixing the nanogels and micelles with 1:1 ratio in neutral conditions (pH=7.4), the composite nanocontainers are positively charged (FIG. 18A), which means that the negatively charged nanogel particles are not enough to neutralize the positively charged micelles. However, a shift in zeta potential towards more positive values, compared to the neutral condition, can still be observed upon decreasing the pH from 7.4 to 6.5. This indicates that the composite nanocontainers made from 1:1 ratio of nanogels and micelles cannot exhibit a charge reversal when decreasing the pH from 7.4 to 6.5. In the case of 7:3 and 9:1 ratios of nanogels and micelles, the as prepared composite nanocontainers are negatively charged (FIGS. 18B and C). This is expected since the quantity of the nanogels bound to the micelle surface is more than enough to neutralize the positive charged micelles. More importantly, after adjusting the pH from 7.4 to 6.5, these two systems switch from negatively charged to a positively charged state.

Thus, the results demonstrate that the composite nanocontainer systems prepared from high nanogel-to-micelle ratio can display charge reversal from negative to positive when changing the system from neutral to weak acid. In other words, coating the positively charged micelles with enough negatively charged nanogels can shield the positive charges in a neutral environment but expose the positive charges in a weak acid environment. Also tested was the zeta potential of the composite nanocontainer system obtained from the copolymer 2 nanogels and PDPA$_{45}$-b-PAMA$_{10}$ micelles. The results, shown in FIG. 18D, further confirm that the charge reversal can only take place when the micelles are coated with sufficient nanogels.

Figure 19:
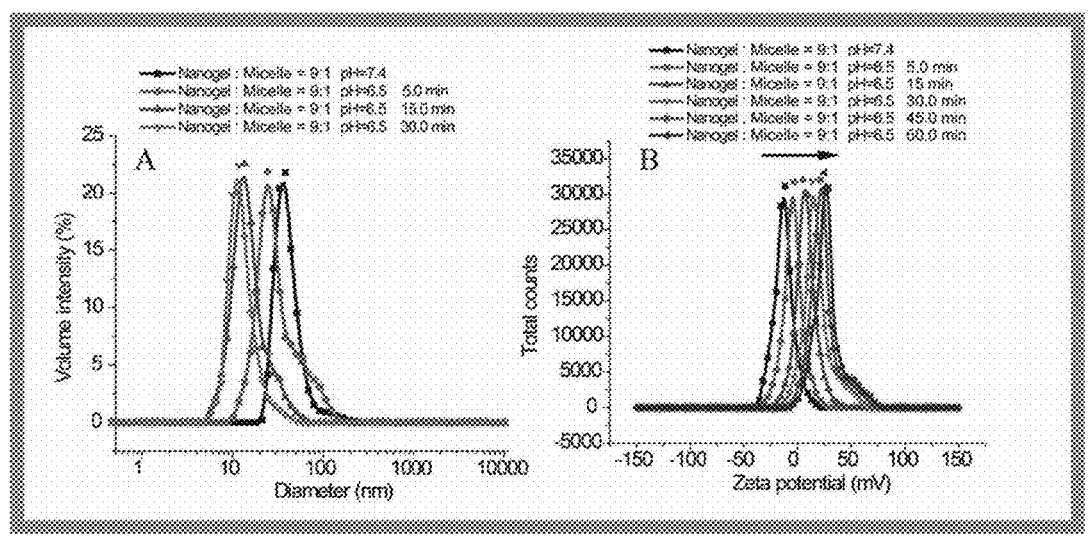
FIG. 19. Disassembly kinetics of the composite nanocontainers in aqueous solution with pH around 6.5 (A); zeta potential changing trend of the composite nanocontainer aqueous solution after decreasing the pH to 6.5 from 7.4 (B). The nanogels (0.5 mg/mL) and the micelles (0.5 mg/mL) used here were made from random copolymer 1 and block copolymer $PDPA_{30}$-b-$PAMA_{15}$.

After decreasing the pH from 7.4 to 6.5, the diameter of the system decreased rapidly, and reached equilibrium within 30 min (FIG. 19A). On the other hand, the change in the zeta potential of the system from negative to positive values was rather gradual and reached equilibrium over 60 minutes (FIG. 19B). In the composite nanocontainer system, weak acid environment leads to the disassembly of the micelles. As a result, the composite nanocontainers dissociate quickly into nanogels and water soluble PDPA-b-PAMA polymer chains, and thereby the system shows a rapid decrease in diameter. However, the dissociated nanogels will further react with the water soluble PDPA-b-PAMA polymer chains because the reaction between amino and epoxy groups can take place easily in weakly acidic solutions. Consequently, the zeta potential of the system keeps on increasing after the complete dissociation of the composite nanocontainers, given that more and more positively charged PDPA-b-PAMA chains are linked on the surface of nanogels.

Encapsulation Stability and Sequential Guest Release

Figure 27:
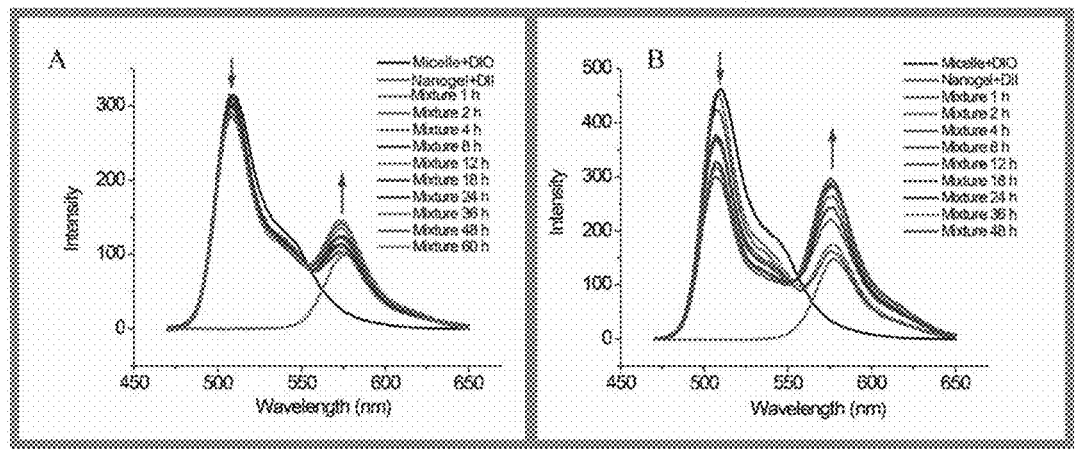
FIG. 27. FRET behavior of the composite nanocontainers (formed from 1:1 ratio of nanogels and micelles) encapsulated with DiO and DiI. The crosslinking percentages of the as used nanogels (copolymer 1, 0.5 mg/mL) were (A) 40%, (B) 20%. Micelles used here are prepared from 0.5 mg/mL of $PDPA_{30}$-b-$PAMA_{15}$. The excitation wavelength of these two systems was 450 nm.

A promising application for these composite nanocontainers is in the field of targeted drug-delivery vehicles. Along with high target-specificity and selectivity, these vehicles need to possess excellent encapsulation stability during circulation. FRET was used to evaluate the encapsulation stability of the composite nanocontainers. (Jiwpanich, et al. 2010 *J. Am. Chem. Soc.* 132, 10683-10685.) A lipophilic FRET pair, 3,3'-dioctadecyloxacarbocyanine perchlorate (DiO, donor) and 1,1'-dioctadecyl-3,3,3',3'-tetramethylindocarbocyanine perchlorate (DiI, acceptor), was chosen for this measurement. The composite nanocontainers were formed from the DiO encapsulated micelles and DiI loaded nanogels. FIGS. 27A and B show the FRET behavior of the composite nanocontainers composed of PDPA$_{30}$-b-PAMA$_{15}$ micelles and nanogels with different crosslinking percentages ($\lambda_{ex}$=450 nm). After mixing the nanogels with the micelles to prepare composite nanocontainers, the intensity of the DiO emission peak at around 480 nm decreased slowly, with a gradual yet concomitant increase in the DiI emission peak at 530 nm. However the FRET ratios after 48 h were still very small, suggesting that the guest interchange speed between the nanogels and the micelles was low. In addition, it can also observed from FIG. 27 that the composite nanocontainers made of 40% crosslinked nanogels show much lower FRET ratio than those composed of 20% crosslinked nanogels. Thus, increasing the crosslinking percentage of the nanogels can improve the encapsulation stability of the composite nanocontainers.

Pyrene and DiI were selected as probes to test the sequential release of different guests from the composite nanocontainers under different stimuli. There is no FRET between pyrene and DiI, which makes the fluorescence intensity reflect the dye concentration more accurately. The guest loaded composite nanocontainers were prepared by encapsulating pyrene and DiI in the micelles and nanogels, respectively.

Figure 20:
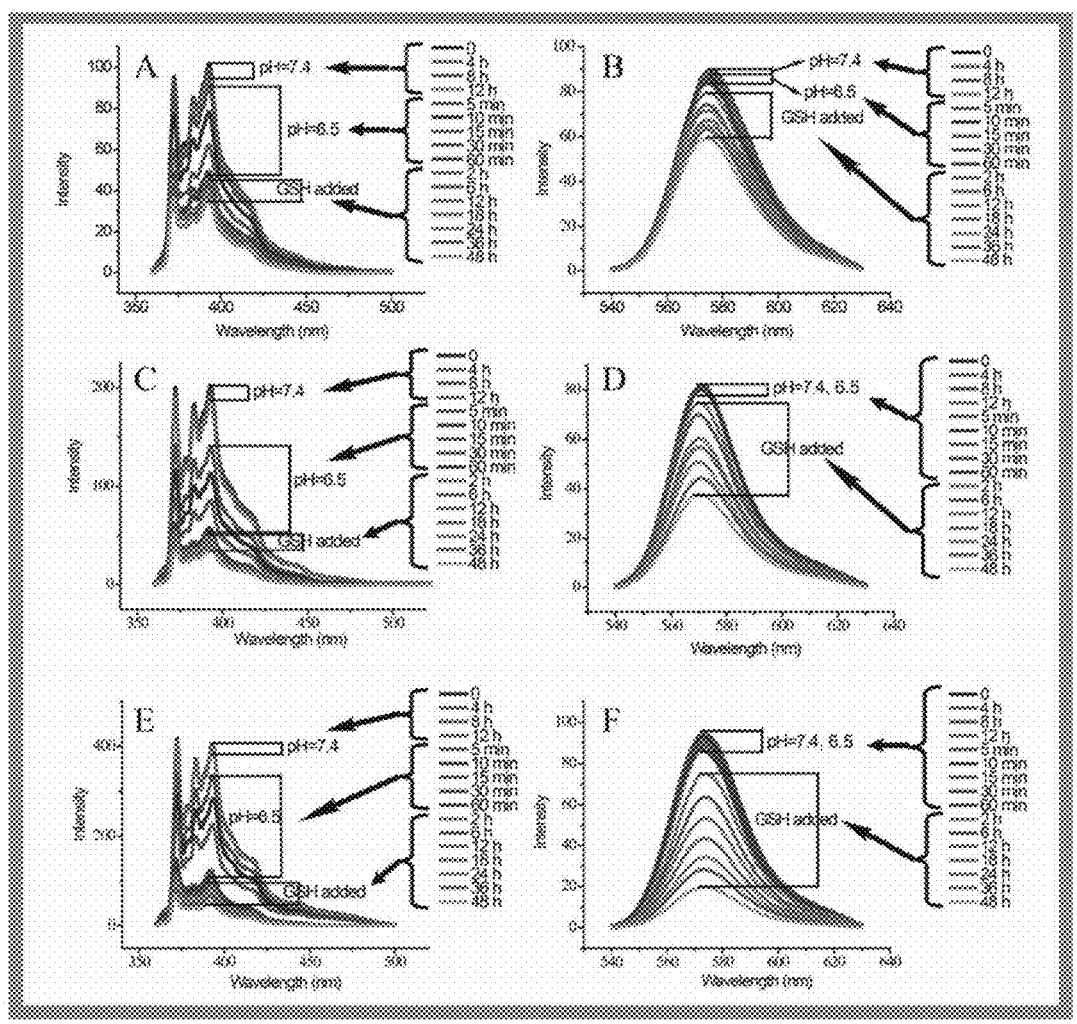
FIG. 20. Fluorescence spectra tracing the sequential release of pyrene and DiI from the composite nanocontainers in response to pH and different concentrations of GSH. (A) and (B) 0.1 mM of GSH, (C) and (D) 5 mM of GSH, (E) and (F) 70 mM of GSH. The composite nanocontainers were constructed by 9:1 ratio of copolymer 1 nanogels (0.5 mg/mL) and $PDPA_{30}$-b-$PAMA_{15}$ micelles (0.5 mg/mL). All the nanogels were 40% crosslinked. Pyrene was encapsulated in the micelles, while the DiI was encapsulated in the nanogels.

Fluorescence spectra of both pyrene (excitation wavelength 334 nm) and DiI (excitation wavelength 530 nm) were recorded simultaneously to monitor the guest release profile under different stimuli. For example, FIGS. 20A and B separately demonstrate the release of pyrene and DiI from the composite nanocontainers. At pH 7.4, the fluorescence intensities of both pyrene and DiI exhibit almost no change, suggesting that the release of the guest molecule cannot take place in a neutral environment. After adjusting the pH of the composite nanocontainer solution to 6.5, it is interesting to find that the fluorescence intensity of pyrene decreases rapidly and significantly in 1 h, while no change can be observed in the DiI fluorescence spectra during this period. Since pyrene was encapsulated in the micelles, we infer that it is the disassembly of micelles, which induces the evident release of pyrene.

GSH (0.1 mM) was then added to the system to further induce the guest release, because the nanogels are redox sensitive and their crosslinked polymer networks can be cleaved off by GSH. As expected, the fluorescence intensity of DiI decreased gradually, indicating a sustained release of DiI guest. At the same period, a slow and slight release of pyrene was observed. This is because a small percentage of the pyrene released in the pH changing period was resorbed by the nanogels. After the decrosslinking of the nanogels, the resorbed pyrene was released along with the DiI.

FIG. 20C-F monitor the sequential release of pyrene and DiI from the composite nanocontainers utilizing higher concentrations of GSH. The changing trends of the fluorescence spectra were almost the same with that given in FIG. 20A, B. However, the stimuli-release of DiI became faster and more significant in higher concentration of GSH, indicating that the releasing speed of DiI depends greatly on the GSH concentration.

Also used were UV/vis spectra to trace the sequential release of pyrene and DiI from the composite nanocontainers. The results shown in FIG. 28 accord well with that illustrated by FIG. 20, which further confirms the achievement of sequential release.

Cellular Uptake

Figure 13:
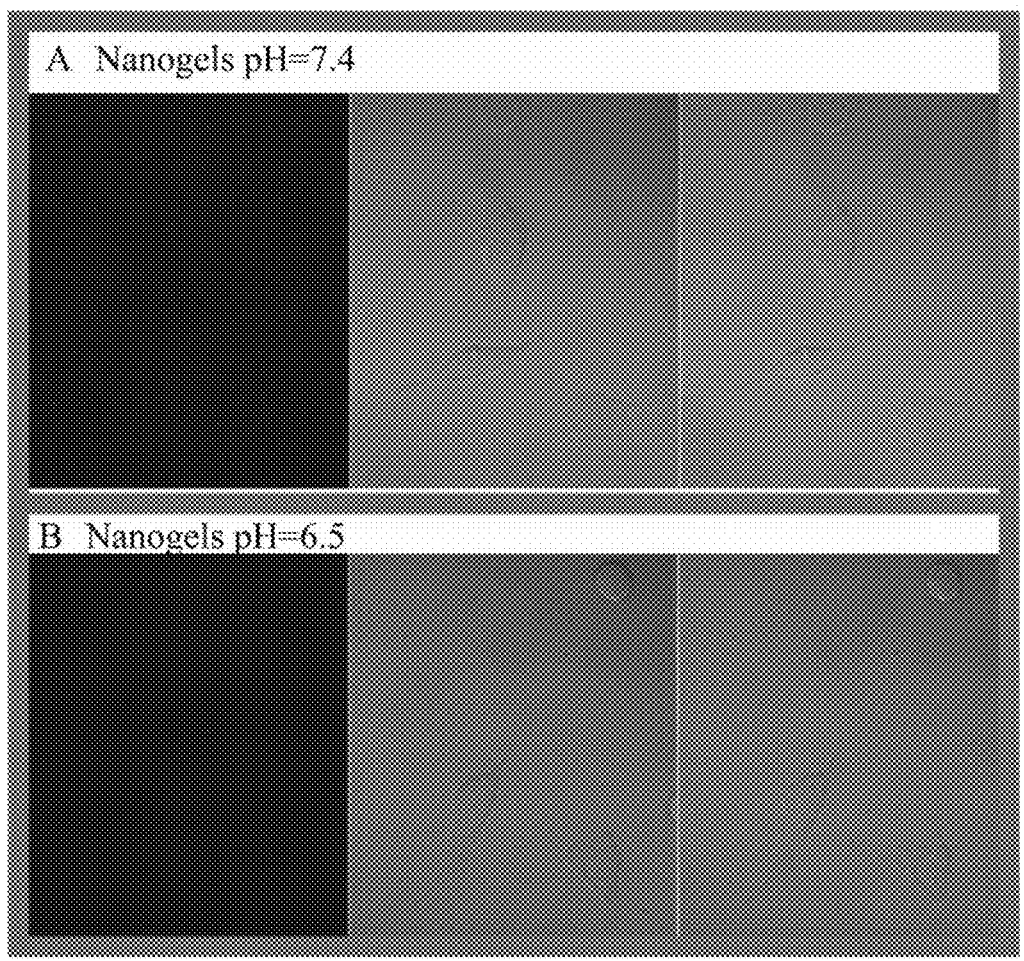
FIG. 13. Cell uptake of nanogels at pH 7.4 and 6.5 after incubation with cells for 30 min. The nanogels used here are made from copolymer 1.

Many nanoscale architectures that positively charged surfaces are capable of being taken up by cells faster than anionic or charge-neutral assemblies. (Du, et al. 2010 *Angew. Chem.*, 21, 3703; He, et al. 2010 *Biomaterials*, 31, 3657.) Note that the surface charge of the composite nanostructure is very similar to that of the nanogel in the 9:1 ratio composite. Therefore at pH 7.4, the composite nanoassembly should not have significant cellular uptake. However, when the pH is reduced at 6.5, the micelle at the core disassembles leaving behind the positively charged protonated tertiary amine block on the surface of the nanogel, which renders the nanogel positively charged (FIG. 3G). Therefore, at this pH the nanocomposite should exhibit a significant cellular uptake. Cellular uptake experiments were performed with HeLa cells for 30 minutes (FIG. 4G and FIG. 4H). No cellular uptake was observed at pH 7.4, whereas significant uptake was observed at pH 6.5. To insure that the nanogels themselves did not have any pH-dependent uptake, control experiments with the nanogels themselves were carried out at both pH's (FIG. 13). There was no discernible cellular uptake of the nanogels under both of these conditions.

Thus, as shown by the exemplary systems disclosed herein, the unique class of composite nanoassemblies and nano-vehicles can separately encapsulate two or more different guests separately and stably, and sequentially deliver them in a controlled fashion triggered by orthogonal stimuli. The invention opens a new window for guest triggered and sequential delivery and establishes a novel route for creating intelligent nano-vehicles in targeted delivery.

Materials and Methods

Materials 2-(Diisopropylamino) ethyl methacrylate (DPA), 2-aminoethyl methacrylate hydrochloride (AMA), copper(I)

bromide (CuBr), 2-propanol (IPA), 2,2'-bipyridine (bpy), pyrene, 2,2'-dithiodipyridine, 2-mercaptoethanol, polyethylene glycol monomethyl ether methacrylate (MW 450), glycidyl methacrylate (GMA), D,L-dithiothreitol (DTT), 3,3'-dioctadecyloxacarbocyanine perchlorate (DiO), 1,1'-dioctadecyl-3,3,3',3'-tetramethylindocarbocyanine perchlorate (DiI), reduced glutathione (GSH), 2,2'-azobis(2-methylpropionitrile) (AIBN), 4-cyano-4-(phenylcarbonothioylthio) pentanoic acid (chain transfer agent) and other conventional reagents were obtained from commercial sources and were used as received unless otherwise mentioned. pyridyl disulfide ethyl methacrylate (PDSEMA) was prepared using a previously reported route. (Ghosh, et al. 2006 *Macromolecules* 39, 5595-5597.) ATRP initiator 1 (FIG. 21) was synthesized according to a reported procedure. (Bontempo, et al. 2004 *J. Am. Chem. Soc.* 126, 15372-15373.)

Synthesis of (PDPA-b-PAMA) Block Copolymer

A series of PDPA-b-PAMA block copolymers with different hydrophobic and hydrophilic chain lengths were synthesized by ATRP polymerization. A typical synthesis of $PDPA_{30}$-b-$PAMA_{15}$ was as follows. Catalyst CuBr (13.0 mg, 0.09 mmol), DPA (0.57 g, 2.7 mmol) and initiator 1 (30.0 mg, 0.09 mmol) were added into a 25 mL flask, which was sealed with a rubber septum. The mixture in the flask was degassed by performing three freeze-pump-thaw cycles. Then a solution of bpy (28 mg, 0.18 mmol) in 0.6 mL of IPA was degassed and injected into the flask under an argon environment. After 5 h polymerization reaction at 50° C., the monomer conversion was higher than 95%. A degassed solution of AMA (0.225 g, 1.35 mmol) in IPA-$H_2O$ (0.36 mL-0.09 mL) was injected into the reaction mixture in argon atmosphere. After 24 h of chain extension polymerization at 50° C., the reaction mixture was diluted with deionized water and dialysed against water (molecular weight cutoff 3500 g $mol^{-1}$) for three days to remove the catalyst and other small molecules. The block copolymer aqueous solution was freeze-dried to obtain the dry product.

Synthesis of Random Copolymer

Polyethylene glycol monomethyl ether methacrylate (1.8 g, 4.0 mmol), PDSEMA (0.76 g, 3.0 mmol), GMA (0.42 g, 3.0 mmol), 4-cyano-4-(phenylcarbonothioylthio) pentanoic acid (28 mg, 0.1 mmol) and 2,2'-azobis(2-methylpropionitrile) (5 mg, 0.03 mmol) were dissolved in 3 mL of tetrahydrofuran. The mixture was poured into a 25 mL flask sealed with a rubber septum. Three freeze-pump-thaw cycles were performed to eliminate the oxygen in the mixture. After 4 h polymerization at 70° C. argon atmosphere, the resultant mixture was dissolved in dichloromethane (5 ml) and precipitated in hexane (200 ml) three times to yield purified copolymer. To obtain copolymer with higher molecular weight, 8 h polymerization time was also used.

Preparation of Micelles

Block copolymers such as $PDPA_{30}$-b-$PAMA_{10}$, $PDPA_{30}$-b-$PAMA_{15}$ and $PDPA_{45}$-b-$PAMA_{10}$ were firstly dissolved in acetone to make solutions with 10 mg/mL concentration. Then the acetone solutions containing the block copolymers were injected into 10 mL of deionized water (with pH around 7.4). The obtained mixtures were left undisturbed at room temperature for 3 days to evaporate the acetone completely, and the micelle aqueous solutions were prepared. To make micelle aqueous solutions with different concentrations, 0.25, 0.5, 1.0 and 2.0 mL of copolymer acetone solutions were also used.

Preparation of Nanogels

In a typical preparation of 40 mol % crosslinked nanogel aqueous solution, 0.5 mL of random copolymer acetone solution (10 mg/mL) solution was injected into 10 mL of deionized water (with pH around 7.4). The obtained mixtures were left undisturbed at room temperature for 3 days to evaporate the acetone completely. DTT (0.15 mg, 0.001 mmol, 20 mol % against PDS groups) was added to crosslink the polymer into nanogel. Unreacted DTT and byproduct pyridothione were removed from the solution by ultrafiltration using a membrane with a molecular weight cutoff of 3,500 g $mol^{-1}$. To prepare 20 mol % crosslinked nanogel, 0.075 mg of DTT was added. Different volumes of random copolymer acetone solution such as 0.25, 1.0 and 2.0 mL were also used to make nanogels with different concentrations.

Encapsulation of Dyes in Micelles and Nanogels

For the preparation of micelles and nanogels encapsulated with dyes (such as DiI, DiO and pyrene), dye acetone solutions (10 mg/mL) were added when injecting block copolymer or random copolymer into deionized water. Other procedures were the same with the preparation of micelle or nanogel aqueous solutions. Excess insoluble dyes were removed by filtration. The dosage of dye used here are 10 wt % of the polymer.

Composite Nanocontainers from the Combination of Micelles and Nanogels

The combination between micelles and nanogels was realized by the surface reaction of amino and epoxy groups, because this reaction can take place even in neutral aqueous solution. A typical combination of micelles with nanogels (mass ratio=1:1) was as follows. 0.5 mL of $PDPA_{30}$-b-$PAMA_{10}$ block copolymer micelle aqueous solution (0.5 mg/mL) and 0.5 mL of crosslinked nanogel (prepared using random copolymer from 6.0 h polymerizaiton) aqueous solution (0.5 mg/mL) were mixed together. The mixture was left undisturbed overnight, to let the micelles combine with nanogels completely. To control the final morphology and property of the composite nanocontainers, various mass ratios of micelle and nanogel such as 3:7 and 1:9, and different concentrations of micelle and nanogel solutions were also adopted. Micelles and nanogels encapsulated with different dyes (such as DII, DIO and pyrene) were also used to make composite nanocontainers loaded with guest molecules.

Characterization $^1$H-NMR spectra were recorded on a 400 MHz Bruker NMR spectrometer with 1000 scans at a relaxation time of 2 s. Molecular weights of the random copolymers were estimated by gel permeation chromatography (GPC) with a refractive index detector using THF as eluent (PMMA was used as standard). Molecular weights of PDPA-b-PAMA block copolymers were measured by aqueous GPC at 35° C. using poly(2-vinyl pyridine) as standard. The eluent was a buffer solution containing 0.30 M $NaH_2PO_4$ and 1.0 M acetic acid (the pH is 3.3). Dynamic light scattering (DLS) and zeta potential measurements were performed using a Malvern Nanozetasizer. The fluorescence spectra were obtained from a JASCO FP-6500 spectrofluorimeter. UV/Vis spectra of the samples in aqueous solutions were measured on a Unico UV/Vis 2802PCS instrument. Transmission electron microscopy (TEM) images were taken from JEOL 100CX at 100 KV.

Sequential Release of Different Dyes from Composite Nanocontainers

Composite nanocontainers with pyren encapsulated in micelles and DiI encapsulated in nanogels were used to evaluate the sequential release of different dyes under different stimuli. The composite nanocontainers loaded with dyes were firstly made in deionized water at pH around 7.4. Then HCl aqueous solution (0.01 mol/L) was used to adjust the solution of composite nanocontainers to 6.5. The fluorescence spectra of the mixture were recorded at regular intervals to monitor the dye release progress. After the release of dyes reached its equilibrium, GSH was added to the mixture. The fluorescence spectra of the mixture were also recorded at regular intervals. UV/Vis spectra were also recorded to trace the release progress after the changing of pH and the addition of GSH.

Cell Uptake Experiments

The nanogels and composite nanoassemblies were tested for the cell uptake study with 40 K HeLa cells per plate. Here the nanogels were loaded with 2 wt % DiI, while the micelles were empty. Before the incubation, the cells are washed thrice with pH 7.4 buffer. 100 μL of 1.0 mg/mL nanogel or composite nanoassembly solution was then incubated in two confocal dishes separately. The pH of the systems was adjusted to 7.4 or 6.5 by buffer solutions. These dishes were incubated for 30 min at 37° C. and washed with 1.0 mL of buffer (pH 7.4) for 5 times and then observed under Zeiss Confocal Microscope with laser excitation at 543 nm.

In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A nano-vehicle carrying two molecular cargos, comprising:
 a first nanoassembly, being a polymeric nanogel of a random copolymer via controlled crosslinking, comprising a first molecular cargo encapsulated stably therein and is individually addressable by a change in redox potential resulting in a structural change therein and release of the first molecular cargo from the first nanoassembly; and
 a second nanoassembly, being a polymeric micelle of a block copolymer, comprising a second molecular cargo encapsulated stably therein and is individually addressable by a change in pH resulting in a structural change therein and release of the second molecular cargo from the second nanoassembly;
wherein
 the block copolymer comprises block of

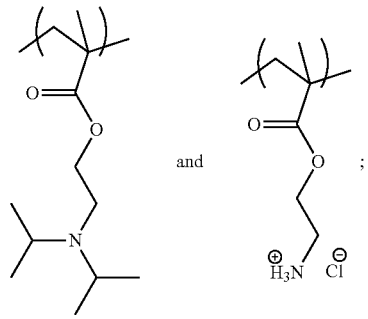

the random copolymer is a copolymer of

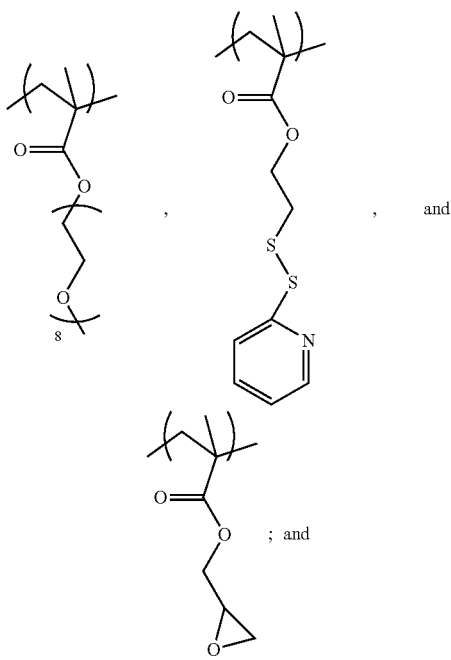

the first nanoassembly and the second nanoassembly are non-covalently or covalently associated in a stoichiometric controlled ratio to form the nano-vehicle, and the first nanoassembly and the second nanoassembly are structurally distinctive at the nanoscale.

2. The nano-vehicle of claim 1, wherein the stoichiometric ratio of the first nanoassembly to the second nanoassembly is from about 1:20 to about 20:1.

3. The nano-vehicle of claim 2, wherein the stoichiometric ratio of the first nanoassembly to the second nanoassembly is from about 1:10 to about 10:1.

4. The nano-vehicle of claim 3, wherein the stoichiometric ratio of the first nanoassembly to the second nanoassembly is about 1:1.

5. The nano-vehicle of claim 1, having a collective diameter from about 10 nm to about 300 nm.

6. The nano-vehicle of claim 2, wherein each of the first nanoassembly is capable of stably encapsulating from about 0.1 wt % to about 25 wt % of the first molecular cargo.

7. The nano-vehicle of claim 2, wherein each of the second nanoassembly is capable of stably encapsulating from about 0.1 wt % to about 25 wt % of the second molecular cargo.

8. A composite nanoassembly comprising two of unit nanoassemblies, wherein each unit nanoassembly type is structurally distinctive at the nanoscale and is individually addressable by biological or chemical intervention resulting in a structural change therein, wherein the biological or chemical intervention for one type of unit nanoassembly is orthogonal to that for other unit nanoassembly types thereby allowing controlled intervention, wherein the first unit nanoassembly type, being a polymeric nanogel of a crosslinked random copolymer, comprises a first guest molecule encapsulated stably therein and is individually addressable by a change in redox potential, and the second unit nanoassembly type, being a polymeric micelle of a block copolymer, comprises a second guest molecule encapsulated stably therein and is individually addressable by a change in pH, wherein the block copolymer comprises block of

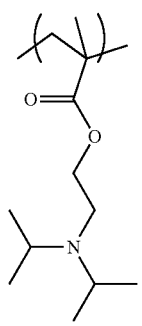 and 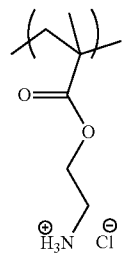 ;  and the random copolymer is a copolymer of

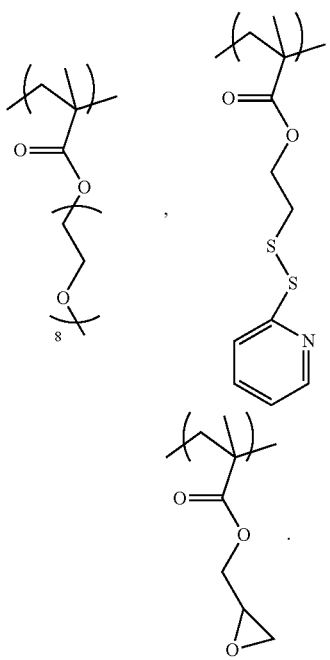

9. The composite nanoassembly of claim 8, wherein each of the first guest molecule and the second guest molecule is selected from a biologically active therapeutic, diagnostic or imaging agent.

10. The composite nanoassembly of claim 9, wherein at least one of the first guest molecule and the second guest molecule is an antitumor agent.

11. The composite nanoassembly of claim 8, wherein the stoichiometric ratio of the first unit nanoassembly type to the second nanoassembly type is from about 1:20 to about 20:1.

12. A method for controlled delivery of two or more distinctive agents to a target biological site, comprising:

providing a composite nanoassembly of claim 8;

delivering the composite nanoassembly to the target biological site;

causing a change in redox potential resulting in a structural change in the first unit nanoassembly type and destabilization of the encapsulation of the first distinctive agent therein, resulting in release of the first distinctive agent therefrom; and causing a change in pH resulting in a structural change in the second unit nanoassembly type and destabilization of the encapsulation of the second distinctive agent therein, resulting in release of the second distinctive agent therefrom.

* * * * *